United States Patent
Charest et al.

(10) Patent No.: US 10,512,717 B2
(45) Date of Patent: Dec. 24, 2019

(54) HEMOTRANSFILTRATION HOLLOW FIBER DEVICE

(71) Applicant: The Charles Stark Draper Laboratory, Inc., Cambridge, MA (US)

(72) Inventors: Joseph L. Charest, Jamaica Plain, MA (US); Christopher M. DiBiasio, Stoughton, MA (US); Violet G. Finley, Medford, MA (US); Jose A. Santos, Westwood, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 94 days.

(21) Appl. No.: 15/606,665

(22) Filed: May 26, 2017

(65) Prior Publication Data

US 2017/0340795 A1 Nov. 30, 2017

Related U.S. Application Data

(60) Provisional application No. 62/342,442, filed on May 27, 2016.

(51) Int. Cl.
*A61M 1/34* (2006.01)
*B01D 63/04* (2006.01)
*B01D 63/02* (2006.01)

(52) U.S. Cl.
CPC .......... *A61M 1/3427* (2014.02); *A61M 1/342* (2013.01); *A61M 1/3413* (2013.01);
(Continued)

(58) Field of Classification Search
CPC .. A61M 1/3413; A61M 1/3431; A61M 1/342; A61M 1/3427; A61M 1/3472; B01D 61/14; B01D 61/142; B01D 63/02; B01D 63/022; B01D 63/04; B01D 63/043; B01D 2313/00; B01D 2313/32; B01D 2313/54;
(Continued)

(56) References Cited

U.S. PATENT DOCUMENTS 4,784,768 A * 11/1988 Mathieu .............. A61M 1/3462
210/321.8
5,176,725 A 1/1993 Puri et al.
(Continued)

FOREIGN PATENT DOCUMENTS

DE 2851929 A1 6/1980
GB 1471936 A 4/1977
(Continued)

OTHER PUBLICATIONS

International Search Report and Written Opinion dated Aug. 28, 2017 in PCT Application No. PCT/US2017/034749.

*Primary Examiner* — Patrick Orme
(74) *Attorney, Agent, or Firm* — McDermott Will & Emery LLP

(57) ABSTRACT

The present disclosure describes a device and method to clear solutes from a patient's blood while maintaining fluid balance. In some implementations, the device and method is used to assist the filtration functions of a patient's liver or kidney. The device includes a plurality of hollow fibers that pass through a sequence of alternating filtration chambers and infusion chambers. The filtration chambers filter the patient's blood while the infusion chambers rehydrate the filtered blood.

11 Claims, 15 Drawing Sheets

(52) U.S. Cl.
CPC ......... *A61M 1/3431* (2014.02); *B01D 63/022* (2013.01); *B01D 63/04* (2013.01); *B01D 63/043* (2013.01); B01D 2313/00 (2013.01); B01D 2313/32 (2013.01); B01D 2313/54 (2013.01)

(58) Field of Classification Search
CPC ............ B01D 2315/16; B01D 2317/02; B01D 2319/00; B01D 2319/02
See application file for complete search history.

(56) References Cited

U.S. PATENT DOCUMENTS

| | | | | |
|---|---|---|---|---|
| 5,700,372 | A | * | 12/1997 | Takesawa ............. A61M 1/342 210/321.6 |
| 2002/0190000 | A1 | * | 12/2002 | Baurmeister ....... A61M 1/3413 210/650 |
| 2004/0200768 | A1 | | 10/2004 | Dannenmaier et al. |

FOREIGN PATENT DOCUMENTS

| | | | |
|---|---|---|---|
| JP | S57-29363 | A | 2/1982 |
| WO | 01/24849 | A1 | 4/2001 |
| WO | 02/26363 | A2 | 4/2002 |

\* cited by examiner

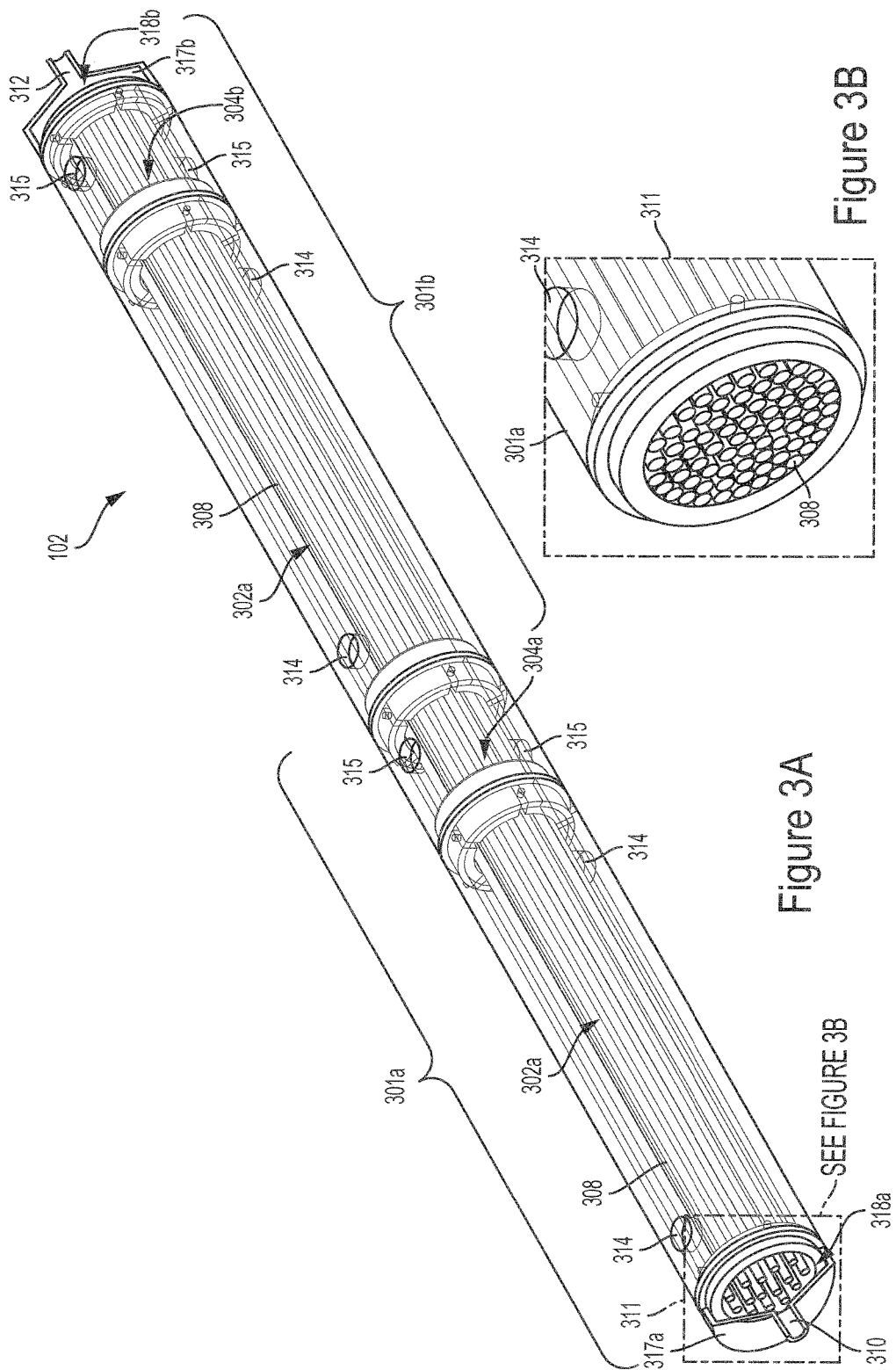

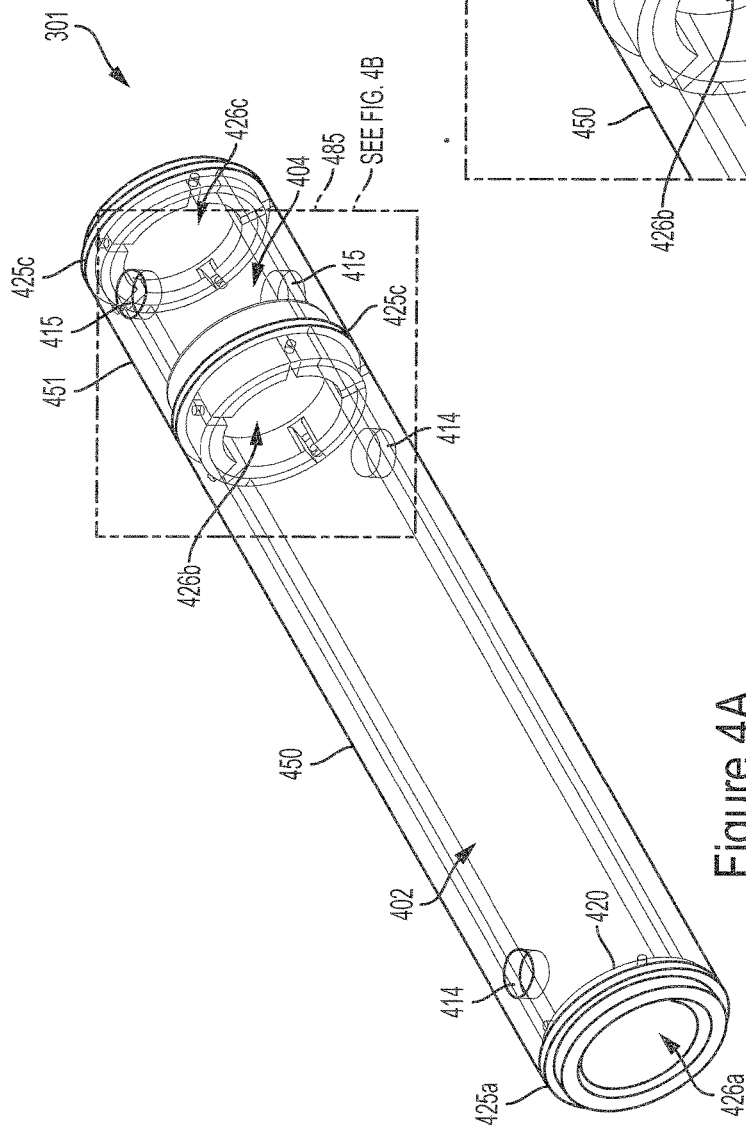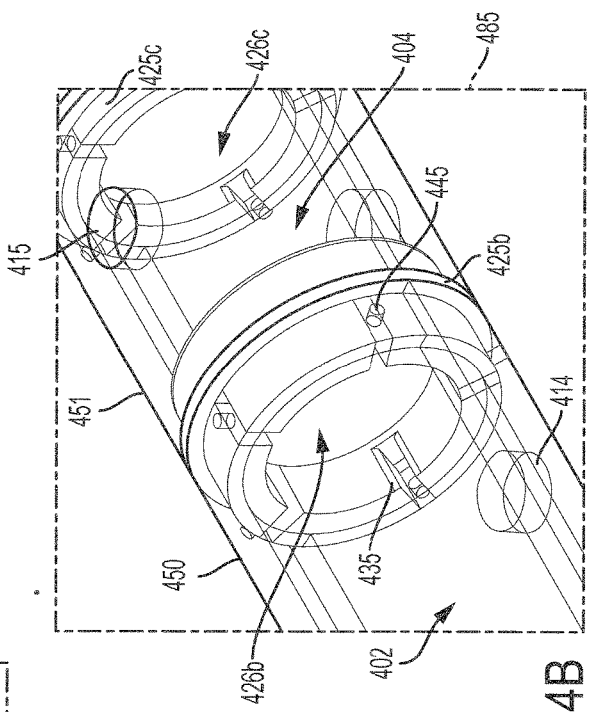
Figure 4A
Figure 4B

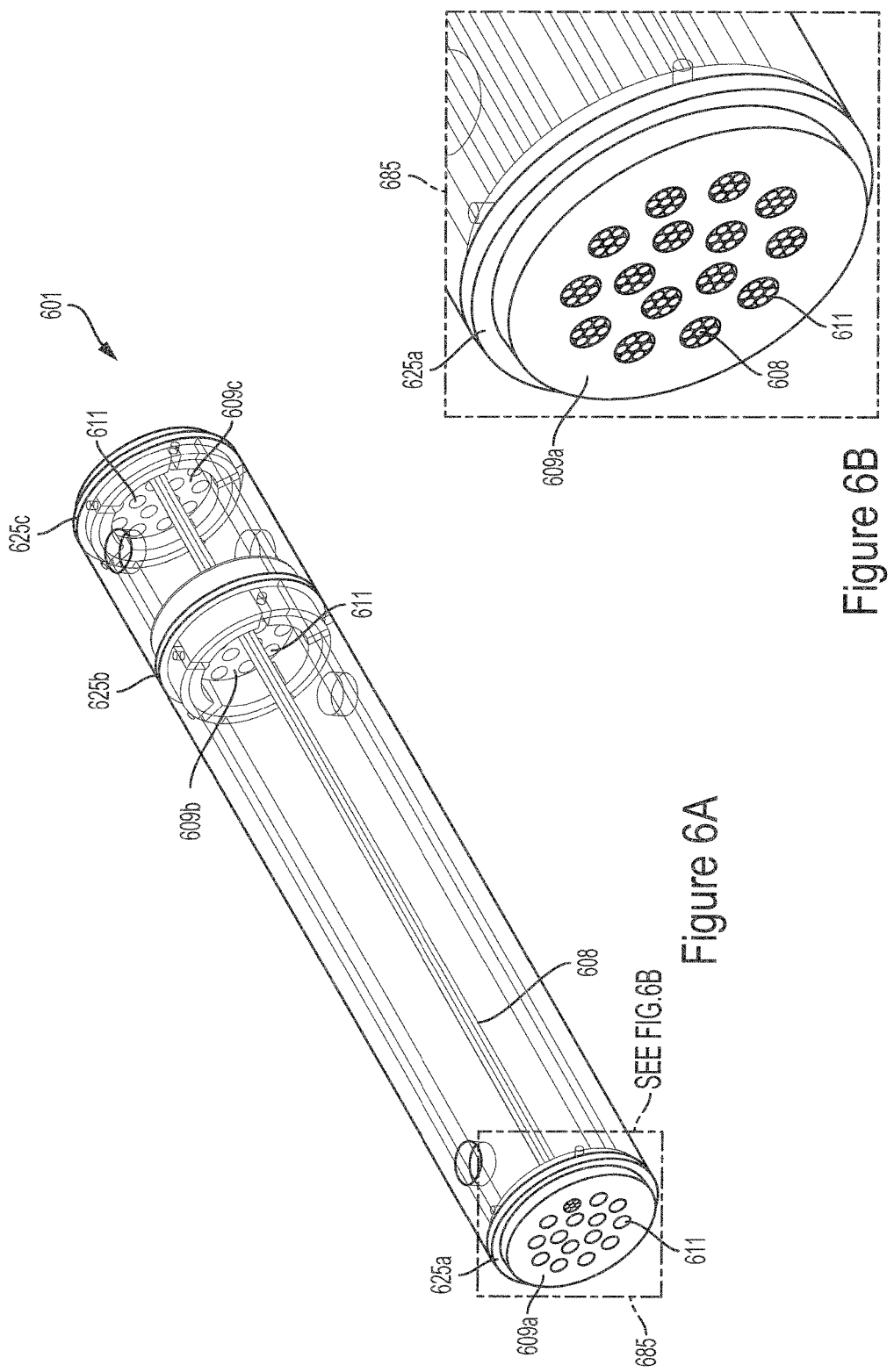

HEMOTRANSFILTRATION HOLLOW FIBER DEVICE

RELATED APPLICATIONS

The present application claims the benefit of, and priority to, U.S. Patent Application No. 62/342,442, titled "HEMOTRANSFILTRATION HOLLOW FIBER DEVICE," and filed on May 27, 2016, the entire contents of which are hereby incorporated by reference.

BACKGROUND

In some hemodialysis devices, the clearance of toxins occurs through diffusion. While diffusion-based clearance can be effective at removing small molecules, larger toxins are not removed as effectively because they diffuse more slowly. The clearance of toxins may also occur through convective clearance. Convective clearance is not heavily affected by molecular size, and therefore removes toxins of all sizes as long as they fall below the cut-off of the filtration membrane. However, convective clearance results in fluid loss from the blood. The loss of fluid from the blood creates a greater concentration of blood cells and proteins within the remaining blood fluid which in turn increases the likelihood of clotting and other damage to the blood cells.

SUMMARY OF DISCLOSURE

According to one aspect of the disclosure, a blood filtration device includes at least one infusate chamber positioned after at least one filtrate chamber along a length of a housing. The device also includes a plurality of hollow fibers that run along the length of the housing. The hollow fibers pass through the at least one filtrate chamber and the at least one infusate chamber. The device also includes at least one wall that separates one of the at least one filtrate chambers from one of the at least one infusate chambers and prevents the passage of fluid between the separated chambers except through the plurality of hollow fibers.

In some implementations, the device comprises a second infusate chamber that is positioned upstream from the at least one filtrate chamber.

In some implementations, the at least one infusate chamber includes a plurality of infusate chambers that are distributed along the length of the housing. At least two of the plurality of infusate chambers are separated by an filtrate chamber of the at least one filtrate chambers. In some implementations, the at least one filtrate chamber includes a plurality of filtrate chambers distributed along the length of the housing. The plurality of hollow fibers passes through the plurality of filtrate chambers and the plurality of infusate chambers.

In some implementations, one of the plurality of infusate chambers separates each of the plurality of filtrate chambers.

In some implementations, each of the at least one wall includes a plurality of holes.

In some implementations, the device may include a plurality of hollow fiber sub-bundles and each hollow fiber sub-bundle may include a subset of the plurality hollow fibers. In some implementations, each hollow fiber sub-bundle passes through one of the holes in the at least one wall. In some implementations, the hollow-fiber sub-bundles each include between about 10 and about 300 hollow fibers.

In some implementations, the plurality of hollow fibers includes a first set of hollow fibers and a second set of hollow fibers and the device includes at least one mixing chamber positioned between one filtrate chamber and one infusate chamber. The device also includes a first set of hollow fibers. At least one of the filtrate chambers and at least one of the infusate chambers is located upstream from the mixing chamber. At least one of the filtrate chambers and at least one of the infusate chambers is located downstream from the mixing chamber. The first set of hollow fibers passes through the at least one filtrate chamber and the at least one infusate chamber located downstream from the mixing chamber. The second set of hollow fibers passes through the at least one filtrate chamber and the at least one infusate chamber located downstream from the mixing chamber.

In some implementations, the plurality of hollow fibers in each chamber includes between about 1,000 and about 15,000 hollow fibers. In some implementations, the plurality of hollow fibers in each chamber includes between about 6,000 and about 15,000 hollow fibers. In some implementations, each of the plurality of filtrate chambers are between about 1 cm and about 20 cm long. In some implementations, each of the plurality of infusate chambers are between about 0.1 cm and about 5 cm long. In some implementations, each of the plurality of hollow fibers includes a permeable wall.

According to another aspect of the disclosure, a method includes flowing blood through a plurality of hollow fibers of a hemotransfiltration device. The method includes generating a first pressure differential in each of one or more filtrate chambers of the hemotransfiltration device such that the first pressure differential results in a flow of fluid and solutes from the blood through walls of the hollow fibers and into the one or more filtrate chambers. The method includes generating a second pressure differential in each of one or more infusate chambers of the hemotransfiltration device such that the second pressure differential results in infusate in the one or more infusate chambers flowing through the walls of the hollow fibers into the blood.

In some implementations, a filtrate pressure in the one or more filtrate chambers is less than a blood pressure within the plurality of hollow fibers passing through the one or more filtrate chambers. In some implementations, an infusate pressure in the one or more infusate chambers is greater than a blood pressure within the plurality of hollow fibers passing through the one or more infusate chambers.

In some implementations, the plurality of hollow fibers of the hemotransfiltration device passes through each of the one or more filtrate chambers and each of the one or more infusate chambers. In some implementations, the device includes a plurality of filtrate chambers each separated by one of the one or more infusate chambers.

In some implementations, the method includes emptying the blood the plurality of hollow fibers into a mixing chamber within the hemofiltration device located between one of the infusate chambers and one of the filtrate chambers. In some implementations, the method includes allowing the blood in the mixing chamber to mix along the length of the mixing chamber. In some implementations, the method includes reintroducing the mixed blood into a second set of hollow fibers and out of the mixing chamber.

In some implementations, flowing the blood into a plurality of hollow fibers includes flowing the blood into a plurality of hollow fiber sub-bundles, each including between about 10 and about 300 hollow fibers.

In some implementations, the hemofiltration device comprises an initial infusate chamber positioned before the plurality of filtrate chambers that are each separated by one of the one or more infusate chambers and flowing blood through the plurality of hollow fibers of the hemotransfiltration device includes pre-diluting the blood prior to the blood in the initial infusate chamber.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which:

FIG. 3A illustrates a perspective view of an example hemotransfiltration device suitable for use as the hemofiltration device in the system shown in FIG. 1 and implemented with identically configured modules.

FIG. 3B illustrates an enlarged view of a portion of the example hemofiltration device illustrated in FIG. 3A.

FIG. 4A illustrates a perspective view of an example module for use in the hemotransfiltration device illustrated in FIG. 3.

FIG. 4B illustrates an enlarged view of a portion of the example module illustrated in FIG. 4A.

FIG. 6A illustrates a perspective view of an example module configured for hollow fiber sub-bundles.

FIG. 6B illustrates an enlarged view of a portion of the example module illustrated in FIG. 6A.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The present disclosure describes a device and method to clear toxins from a patient's blood while maintaining fluid balance. In some implementations, the device and method may clear a plurality of solutes from a patient's blood. In some implementations, the solutes may be toxins, small proteins or peptides, or other molecules, such as beta-2-microglobulin (B2M). In some implementations, the device is used to assist the filtration and/or blood processing functions of a patient's liver or kidney. The device includes at least one set of alternating filtration and infusion segments that filter and rehydrate the blood.

The device uses convective clearance to provide increased filtration and/or blood processing compared to diffusion-based clearance devices. It should be noted that some diffusive clearance will occur in the device if a concentration gradient exists and a diffusive clearance mechanism could increase the overall ability of the device to clear solutes. While diffusion-based clearance can be effective at removing small molecules, larger solutes are not removed as effectively because they diffuse more slowly. Convective clearance is not heavily affected by molecular size, and therefore removes solutes of all sizes as long as they fall below the cut-off of the filtration membrane.

Current hemofiltration devices (devices which typically employ only filtration and little to no diffusion-based clearance) typically are limited to a 20% filtration fraction when blood is not diluted until exiting the device (post-dilution hemofiltration). The filtration fraction is defined as the flow rate of filtration divided by the flow rate of the blood through the device. Devices described herein incorporate at least one infusion chambers and at least one filtration chamber. The combination of infusion and filtration chambers enables better control of blood concentration and can eliminate the filtration fraction limits exhibited by many current hemofiltration devices. This in turn allows the clearance of solutes from the blood to be fully, or at least primarily, convective-based and therefore clears larger sized solutes much more effectively than current hemofiltration devices.

Figure 1:
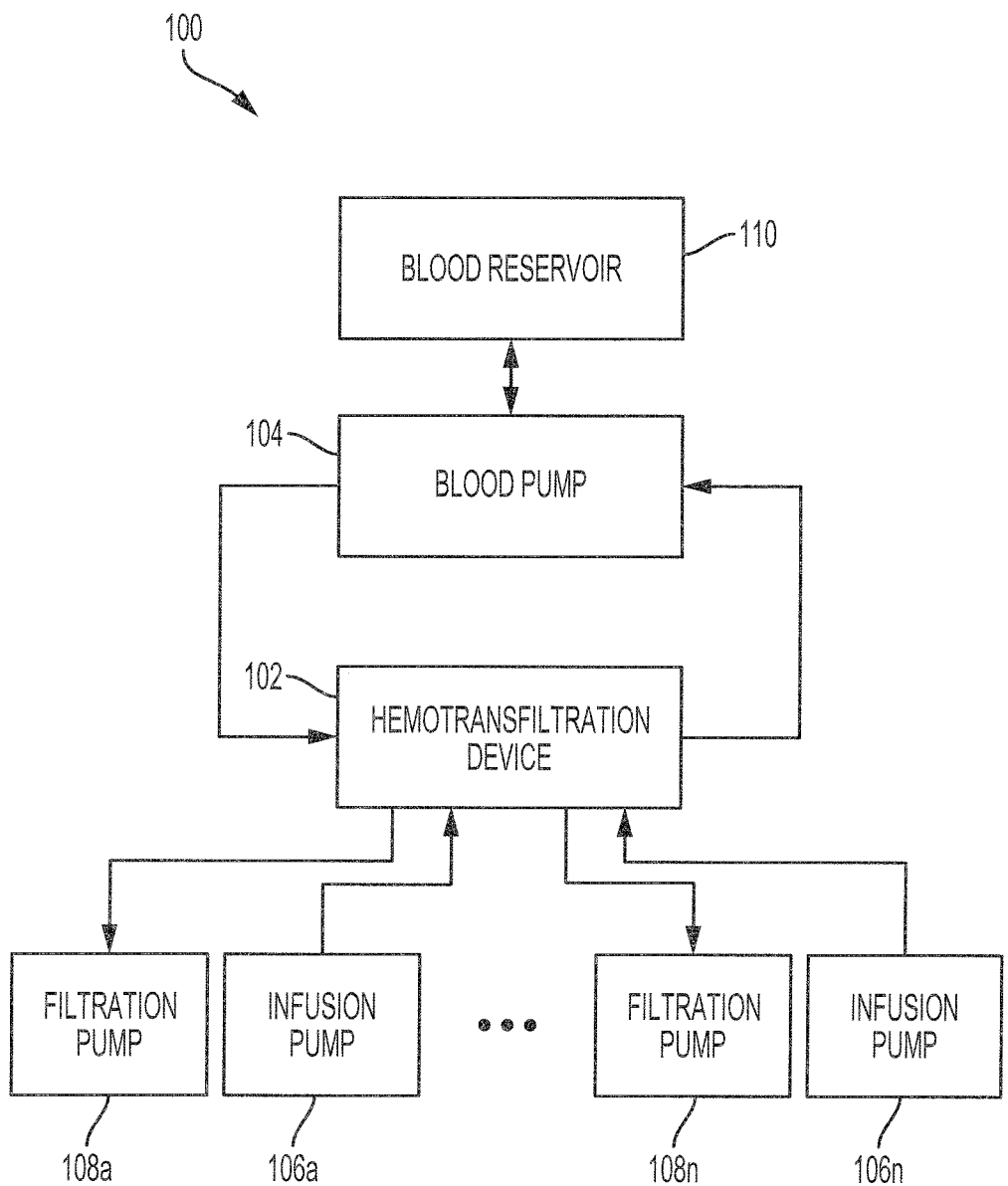
FIG. 1 illustrates an example system for filtering a patient's blood.

FIG. 1 illustrates an example system 100 for filtering a patient's blood. The system 100 includes a hemotransfiltration device 102. The blood pump 104 pumps blood through the hemotransfiltration device 102. The system 100 includes a plurality of infusion pumps 106a-106n that pump infusate into the hemotransfiltration device 102 and a plurality of filtrate pumps 108a-108n that draw filtrate out of the hemotransfiltration device 102. The system 100 also includes a blood reservoir 110.

As an overview, the hemotransfiltration device 102 includes a plurality of hollow fibers that, in some implementations, run the length of the hemotransfiltration device 102. The hollow fibers pass through a sequence of alternating filtration segments and infusate segments along the length of the device 102. The blood pump 104 pumps blood from the blood reservoir 110 to, and through, the hollow fibers of the hemotransfiltration device 102. As the blood flows through the hollow fibers in each of the filtration segments, fluid and solutes such as peptides, proteins, toxins and other molecules, such as beta-2-microgloubulin (B2M) are removed from the blood through convective clearance. As the blood flows through the hollow fibers in each of the infusion segments, clean fluid is infused through the walls of the hollow fibers and into the blood. In some implementations, the pattern of filtering the blood through convective clearance and infusing fluid into the blood is repeated a number of times along the length of the hemotransfiltration device 102. Because fluid loss resulting from the convective clearance of the blood in the filtration segments is replaced in a neighboring infusion segment, the filtration fraction can be as high as (or even higher than) 100% (e.g., all the fluid in the blood can be replaced with fresh fluid by the end of the hemotransfiltration device 102).

The system 100, as illustrated in FIG. 1, includes a blood pump 104 for moving the blood from the blood reservoir 110 and through the hemotransfiltration device 102. In some implementations, the fluidic circuit between the blood pump 104 and the hemotransfiltration device 102 includes a patient in place of, or in addition to, the blood reservoir 110. For example, the blood pump 104 can extract blood from a patient, flow the blood through the hemotransfiltration device 102, and then return the blood to the patient. In some implementations, the blood pump 104 operates continuously, while in other implementations the blood pump 104 works intermittently, and only activates when the level of whole blood in the hemotransfiltration device 102, or a manifold leading thereto, falls below a set threshold. In some implementations, the flow rate of the blood pump 104 is configurable. In some implementations, the flow rate and/or the pressure of the blood is monitored as the blood flows through the hemotransfiltration device 102. These measurements in turn are used by a controller to control the flow rate of the blood pump 104. Example pumps can include, but are not limited, to peristaltic pumps, impeller pumps, or any other pump suitable for flowing blood.

The system 100 also includes one or more of filtration pumps 108 and infusion pumps 106. The filtration pumps 108 are configured to control the flow of filtrate into or out of each of the filtrate chambers of the hemotransfiltration device 102. The infusion pumps 106 are configured to control the flow of infusate into or out of each of the infusate chambers. In some implementations, the infusion pumps 106 are configured to pressurize the infusate chambers such that the infusate is at a higher relative pressure compared to the blood within the hollow fibers passing through the infusate chambers. The filtration pumps 108 are configured to draw filtrate out of the filtrate chambers such that the filtrate is at a lower relative pressure compared to the blood within the hollow fibers passing through the filtrate chambers. The pressure difference created by the respective pumps causes fluid (and solutes such as molecules of peptides, proteins, toxins and other molecules such as beta-2-microgloubulin (B2M)) to pass from the blood to the filtrate of the filtrate chambers. In the infusate chambers, the pressure difference drives infusate into the blood in the hollow fibers.

In some implementations, each of the filtrate chambers of the hemotransfiltration device 102 is coupled to a respective filtration pump 108, and each of the infusate chambers is coupled to a respective infusion pump 106. In other implementations, a single filtration pump 108 is coupled to multiple (and in some cases all) of the filtrate chambers and a single infusion pump 106 is coupled to multiple (and in some cases all) of the infusate chambers. In some implementations, fluid resistors are built into the fluid connections between the chambers and the respective filtration pumps 108 or infusion pumps 106 to control the flow rate into or out of the chambers.

As mentioned above, the filtration pumps 108 are configured to control the flow of filtrate into or out of each of the filtrate chambers of the hemotransfiltration device 102. As also mentioned above, the infusion pumps 106 are configured to control the flow of infusate into or out of the infusate chambers of the hemotransfiltration device 102. In some implementations, the filtration pumps 108 are configured to drive filtrate into and draw filtrate out of each of the filtrate chambers of the hemotransfiltration device 102. In some implementations, the infusion pumps 106 are configured to drive infusate into and draw infusate out of each of the infusate chambers of the hemotransfiltration device 102. In some implementations, the filtrate is driven into the filtrate chambers and is intermittently replaced in order to avoid an equilibrium state. For example, the fluid in the filtration chambers may be intermittently replaced about every 10 minutes.

Figure 2:
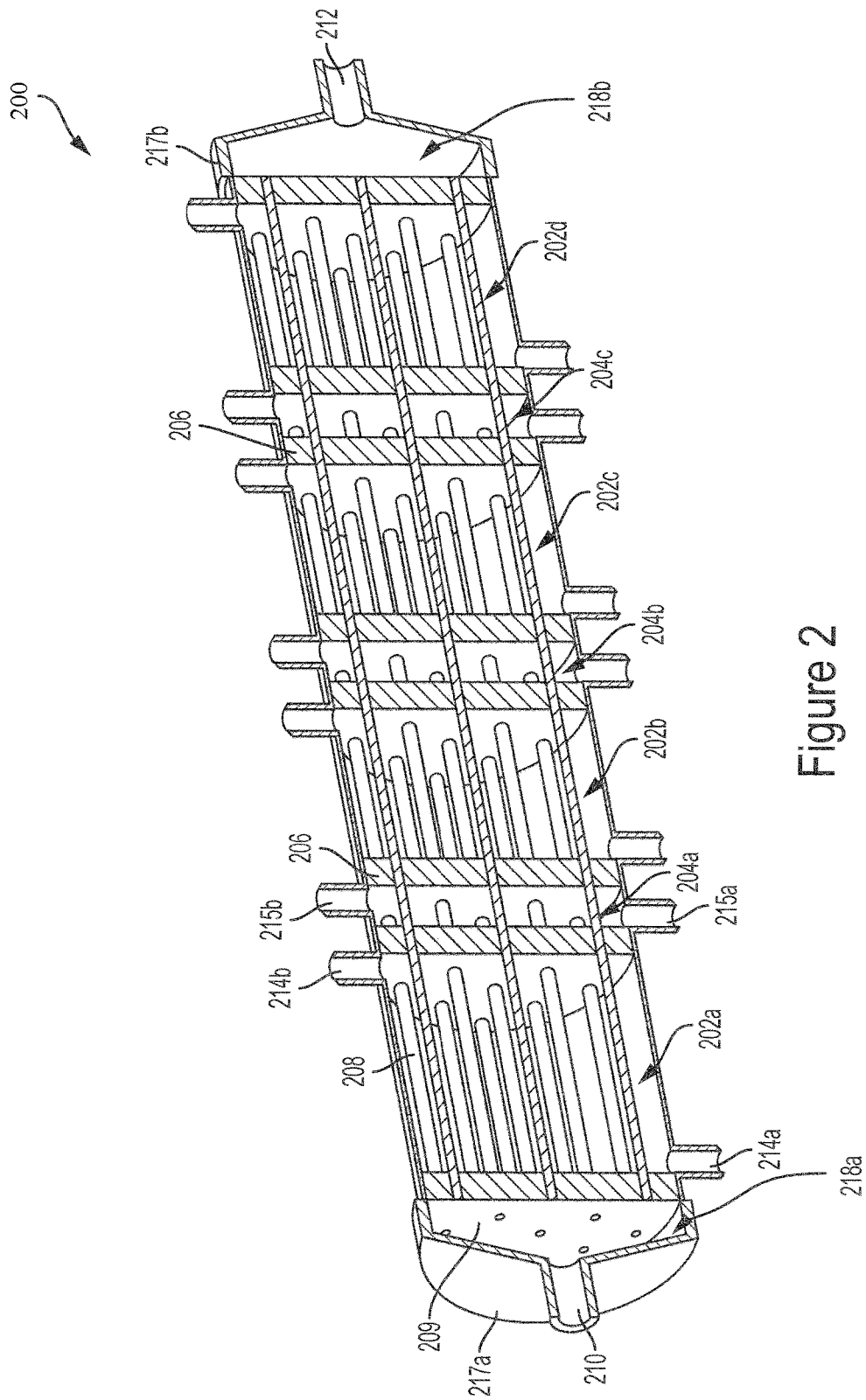
FIG. 2 illustrates a cut-away view of an example hemotransfiltration device suitable for use as the hemofiltration device in the system shown in FIG. 1.

FIG. 2 illustrates a cut-away view of an example hemotransfiltration device 200 suitable for use as the hemofiltration device 102 the system 100. The device 200 includes a sequence of alternating filtration chambers and infusion chambers distributed along the length of the housing of the device 200. The hemotransfiltration device 102 includes a plurality of filtrate chambers such a first filtrate chamber 202a, a second filtrate chamber 202b, a third filtrate chamber 202c and a fourth filtrate chamber 202d (collectively referred to as filtrate chambers 202). The filtrate chambers 202 are distributed along a length of the housing of the device 200. The device 200 also includes a plurality of infusate chambers such as a first infusate chamber 204a, a second infusate chamber 204b, a third infusate chamber 204c and a fourth infusate chamber 204d (collectively referred to as infusate chambers 204). The infusate chambers 202 are distributed along a length of the housing of the device 200. As shown in FIG. 2, each of the infusate chambers 204 is positioned after a respective filtrate chamber 202 along the length of the housing of the device 200. In some other implementations, a first chamber may serve as an infusate chamber 204 to pre-dilute the blood in the hollow fibers prior to the blood entering a first filtrate chamber 202. In some implementations, the hemotransfiltration device 200 includes between about one about and about ten filtrate chambers 202, between about one and about eight filtrate chambers 202, or between about three and about six filtrate chambers 202. In some implementations, the number of filtrate chambers 202 may be different from the number of infusate chambers 204.

A plurality of hollow fibers 208 run along the length of the hemotransfiltration device 200 passing through the filtrate chambers 202 and the infusate chambers 204. For illustrative purposes, FIG. 2 shows only 18 hollow fibers 208. However, in some implementations, the hemotransfiltration device 200 can include between about 1,000 and about 50,000 hollow fibers 208, between about 1,000 and about 35,000 hollow fibers 208, between about 5,000 and about 20,000 hollow fibers 208, between about 1,000 and about 6,000 hollow fibers 208 or between about 6,000 and 15,000 hollow fibers 208. In some implementations, the hollow fibers 208 have a length between about 5 cm and about 80 cm, between about 20 cm and about 70 cm, or between about 30 cm and about 60 cm.

The walls of the hollow fibers 208 are permeable. The walls of the hollow fibers 208 are configured to enable fluid and solutes to pass from the blood and into the filtrate within the filtrate chambers 202 and to allow infusate to flow into the hollow fibers 208 within the infusate chambers 204. In some implementations, the solutes may be peptides, proteins, toxins or other molecules. In some implementations, the wall of the hollow fibers 208 is between about 20 μm and about 75 μm or between about 30 μm and about 50 μm thick. Each of the hollow fibers 208 have an inner diameter between about 50 μm and about 300 μm or between about 100 μm and about 250 μm.

The hemotransfiltration device 200 also includes a plurality of walls 206 located along the length of the housing of the device 200. The walls 206 separate the filtrate chambers 202 from the infusate chambers 202. In some implementations, the walls 206 define the lengths of the filtrate chambers 202 to be between about 1 cm and about 20 cm, between about 5 cm and about 20 cm, or between about 10 cm and about 20 cm. In some implementations, the walls 206 define the length of the infusate chambers 204 to be between about 0.1 cm and about 5 cm or between about 1 cm and about 2 cm.

The walls 206 also separate the filtrate chambers 202 from their neighboring infusate chambers 204. The walls 206 are configured to enable a plurality of hollow fibers 208 to pass between the filtrate chambers 202 and the infusate chambers 204. In some implementations, the filtrate chambers 202 and the infusate chambers 204 are formed by inserting the plurality of hollow fibers 208 through a plurality of holes in a solid material such that the hollow fibers 208 seal against the solid material. In some implementations, the solid material can be a potting compound. In some implementations, the walls 206 are injection molded, milled, or cast. The thickness of the walls 206 determines the level of mixing achieved in the infusate chambers 304 between the infusate and the blood. In some implementations, the thickness of the walls 206 is between about 3 mm and about 2 cm.

The device 200 includes an endcap on each end through which blood enters and exits the device 200. The device 200 includes a first endcap 217a and a second endcap 217b (collectively referred to as endcaps 217), each located on opposite ends of the device 200. The first endcap 217a includes an inlet 210 and the second endcap 217b includes an outlet 212. Blood enters the hemotransfiltration device 200 through the inlet 210 of the first endcap 217a and exits the device 200 through the outlet 212 of the second endcap 217b.

Blood enters the hemotransfiltration device 200 through the inlet 210 of the first endcap 217a and passes through the hollow fibers 208 running along the length of the filtrate chambers 202 and the infusate chambers 204. As the blood flows through the hollow fibers 208 in the filtrate chambers 202, fluid and solutes such as molecules of toxins, peptides, proteins and/or other molecules such as beta-2-microglobulin (B2M) are removed or cleared from the blood through convective clearance. As the blood flows through the hollow fibers 208 in the infusate chambers 204, clean fluid is infused through the walls of the hollow fibers 208 and into the blood. The blood passes through and out of the hollow fibers 208 in the fourth filtrate chamber 202d and exits the device 200 through the outlet 212 of the second endcap 217b.

In some implementations, the first endcap 217a may define a first plenum 218a located between the first endcap 217a and the wall 206 of the first filtrate chamber 202a. In such implementations, the blood enters the device 200 through the inlet 210 of the first endcap 217a and mixes within the first plenum 218a before passing into and through the hollow fibers 208 in the first filtrate chamber 202a. In some implementations, the second endcap 217b may define a second plenum 218b located between the wall 206 of the fourth infusate chamber 204d and the second endcap 217b. In such implementations, the blood passes through and out of the hollow fibers 208 in the fourth infusate chamber 204d and mixes within the second plenum 218b before exiting the device 200 through the outlet 212 of the second endcap 217b. In some implementations, the length of the first and second plenum may be between about 1 mm to about 2 cm.

Filtrate and infusate flow into or out of the device 200 via a plurality of ports. Each of the filtrate chambers 202 includes a plurality of ports such as a first filtrate chamber port 214a and a second filtrate chamber port 214b (collectively referred to as filtrate chamber ports 214). Each of the infusate chambers 204 includes a plurality of ports such as a first infusate chamber port 215a and a second infusate chamber port 215b (collectively referred to as infusate chamber ports 215).

As mentioned above, the system 100 can include a plurality of filtrate pumps 108 and a plurality of infusion pumps 106. Each of the filtrate chambers 202 are coupled to their respective filtration pumps 108 via the filtrate chamber ports 214. Each of the infusate chambers 204 are coupled to their respective infusion pumps 106 via the infusate chamber ports 215. In some implementations, during operation of the hemotransfiltration device 200 in the system 100, one of the filtrate chamber ports 214 is closed while the other is coupled to one of the plurality of filtration pumps 108. In such implementations, one of the infusate chamber ports 215 is also closed while the other is coupled to one of the plurality of infusion pumps 106. The closed port of the two filtrate ports 214 to each of the filtrate chambers 202 and the closed port of the two infusate chambers 204 can be opened to prime the respective chambers 202 or 204 of the hemotransfiltration device 200 with liquid. In some implementations, the filtrate or infusate may flow into and out of the respective filtrate or infusate chambers 202 and 204 of the device 200 via a single port in an intermittent fluid replacement mode of operation. In such implementations, each of the filtrate chambers 202 may include a single filtrate chamber port 214 and each of the infusate chambers 204 may include a single infusate chamber port 215.

The hemofiltration devices described herein may be implemented according to a variety of modular designs. Referring back to FIG. 2, the hemofiltration device 200 may be implemented using a single cylindrical (or substantially cylindrical) tube that is segmented into alternating filtrate chambers 202 and infusate chambers 204 by a plurality of walls 206. In some implementations, a hemofiltration device for use as the hemofiltration device 102 in the system 100 may be implemented by using a plurality of identically configured modules. FIG. 3 illustrates a perspective view of a hemotransfiltration device 300 suitable for use as the hemofiltration device 102 in the system 100 illustrated in FIG. 1 and implemented using identically configured modules. The hemotransfiltration device 300 includes a pair of identically configured modules such as a first chamber module 301a and a second chamber module 301b (collectively referred to as chamber modules 301). Each of the chamber modules 301 includes a pair of chambers. The first chamber module 301a includes a first filtration chamber 302a and a first infusate chamber 304a. The second chamber module 301b includes a second filtrate chamber 302b and a second infusate chamber 304b. The first filtration chamber 302a, the first infusate chamber 304a, the second filtration chamber 302b and the second infusate chamber 304b are distributed along the length of the device 300. The chamber modules 301 are arranged such that each of the infusate chambers 304 follows a respective filtrate chamber 302 along the length of the housing of the device 300

Although the device 300 is shown having two chamber modules 301a and 301b, the device 300 can include any number of chamber modules 301 serially connected along the length of the device 300. In some implementations, the chamber modules 301 may be arranged such that each of the infusate chambers 304 is followed by a respective filtrate chamber 302 along the length of the housing of the device 300. In some implementations, the hemotransfiltration device 300 includes between about one about and about ten filtrate chambers 302, between about one and about eight filtrate chambers 302, or between about three and about six filtrate chambers 302. In some implementations, the number of filtrate chambers 302 may be different from the number of infusate chambers 304. In some other implementations, the device 300 may include a first chamber that serves as an infusate chamber 304 to pre-dilute the blood in the hollow fibers prior to the blood entering a first filtrate chamber 302.

The hemofiltration device 300 includes a bundle of open-ended hollow fibers 308 running along the length of the first chamber module 301a and the second chamber module 301b passing through the first filtrate chamber 302a, the first infusate chamber 304a, the second filtrate chamber 302b and the second infusate chamber 304b. As shown in FIG. 3, on one end of the device 300, the ends of the hollow fibers 308 align with an opening of the first chamber module 301a. On the opposite end of the device 300, the ends of the hollow fibers 308 align with an opening of the second chamber module 301b. FIG. 3B illustrates an enlarged view of a portion 311 of the example hemofiltration device illustrated in FIG. 3A. FIG. 3B shows the open ends of the hollow fibers 308 aligned with an opening of the first chamber module 301a.

As mentioned above, a plurality of hollow fibers 308 run along the length of the hemotransfiltration device 300 passing through the filtrate chambers 302 and the infusate chambers 304. In some implementations, the hemotransfiltration device 300 can include between about 1,000 and about 50,000 hollow fibers, between about 1,000 and about 35,000 hollow fibers, between about 5,000 and about 20,000 hollow fibers or between about 6,000 and 15,000 hollow fibers. In some implementations, the hollow fibers 308 have a length between about 5 cm and about 80 cm, between about 20 cm and about 70 cm, or between about 30 cm and about 60 cm.

The walls of the hollow fibers 308 are permeable. The walls of the hollow fibers 208 are configured to enable fluid and solutes to pass from the blood and into the filtrate within the filtrate chambers 302 and infusate into pass into the hollow fibers 308 within the infusate chambers 304. In some implementations, the wall of the hollow fibers 308 is between about 20 µm and about 75 µm or between about 30 µm and about 50 µm thick. Each of the hollow fibers 308 have an inner diameter between about 50 µm and about 300 µm or between about 100 µm and about 250 µm.

The hemofiltration device 300 includes a first endcap 317a and a second endcap 317b (collectively referred to as endcaps 317), each located at opposite ends of the device 300. The first endcap 317a includes an inlet 310 and the second endcap 317b includes an outlet 312. Blood enters the hemotransfiltration device 300 through the inlet 310 of the first endcap 317a and exits the device 300 through the outlet 312 of the second endcap 317b. Blood enters the hemotransfiltration device 300 through the inlet 310 of the first endcap 317a and passes through the hollow fibers 308 running along the length of the first chamber module 301a. As the blood flows through the hollow fibers 308 in the first and second filtrate chambers 302a and 302b of the first and second chamber modules 301a and 301b, fluid and solutes are removed or cleared from the blood through convective clearance. As the blood flows through the hollow fibers 308 in the first and second infusate chambers 304a and 304b of the first and second chamber modules 301a and 301b, clean fluid is infused through the walls of the hollow fibers 308 and into the blood. The blood passes through and out of the hollow fibers 308 and exits the device 102 through the outlet 312 of the second endcap 317b.

In some implementations, the first endcap 317a may define a first plenum 318a located between the first endcap 317a and the opening of the first chamber module 301a. In such implementations, the blood enters the device 300 through the inlet 310 of the first endcap 317a and mixes within the first plenum 318a before passing into and through the hollow fibers 308 in the first filtrate chamber 302a of the first chamber module 301a. In some implementations, the second endcap 317b may define a second plenum 318b located between the second endcap 317b and the opening of the second chamber module 301b. In such implementations, the blood passes through and out of the hollow fibers 308 in the second infusate chamber 302b of the second chamber module 301b and mixes within the second plenum 318b before exiting the device 300 through the outlet 312 of the second endcap 317b. In some implementations, the lengths of the first and second plenum may be between about 1 mm to about 2 cm. In some implementations, the open ends of the hollow fibers 308 may not align exactly with the openings of the chamber modules 301. For example, a portion of the hollow fibers 308 may extend out of the openings 326a and 326b into the respective plenum 318a or 318b.

Referring back to FIG. 3, filtrate and infusate flow into or out of the device 300 via a plurality of ports. Each of the filtrate chambers 302 includes a pair of filtrate chamber ports 314. Each of the infusate chambers 304 includes a pair of infusate chamber ports 315. As mentioned above, the system 100 includes one or more filtrate pumps 108 and one or more infusion pumps 106. Each of the filtrate chambers 302 can be coupled to the same or a different filtration pump 108 via the filtrate chamber ports 314. Each of the infusate chambers 304 can be coupled to the same or a different infusion pump 106 via the infusate chamber ports 315. In some implementations, during operation of the hemotransfiltration device 300 in the system 100, one of the filtrate chamber ports 214 is closed while the other is coupled to one of the plurality of filtration pumps 108. In such implementations, one of the infusate chamber ports 315 is also closed while the other is coupled to one of the plurality of infusion pumps 106. The closed port of the two filtrate ports 314 to each of the filtrate chambers 302 and the closed port of the two infusate chambers 304 can be opened to prime the respective chambers 302 or 304 of the hemotransfiltration device 300 with liquid. In some implementations, the filtrate or infusate may flow into or out of the respective filtrate or infusate chambers 302 and 304 of the device 300 via a single port. In such implementations, each of the filtrate chambers 302 may include a single filtrate chamber port 314 and each of the infusate chambers 304 may include a single infusate chamber port 315.

FIG. 4A illustrates a perspective view of the module 301 used in the hemotransfiltration device 300 illustrated in FIG. 3. The housing of the module 301 is a hollow open-ended cylinder that is segmented along its length into a first cylinder 450 and a second cylinder 451. The first cylinder 450 defines a first chamber 402 and includes a pair of first chamber ports 414. The second cylinder 451 defines a second chamber 404 and includes a pair of second chamber ports 415. In some implementations, each of the first and second cylinders 450 and 451 may be manufactured as two half cylinders which are adhered to each other to form a full cylinder.

The module 301 includes a plurality of annular baffles such as a first annular baffle 425a, a second annular baffle 425b and a third annular baffle 425c The first annular baffle 425a is coupled to a first end of the first cylinder 450 forming a first opening 426a in the module 301. The second annular baffle 425b is coupled to a second end of the first cylinder 450 and a first end of the second cylinder 451 forming a second opening 426b in the module 301. The third annular baffle 425c is coupled to a second end of the second cylinder 451 forming a third opening 426c in the module 301.

FIG. 4B illustrates an enlarged view of a portion 411 of the example module 301 illustrated in FIG. 4A. FIG. 4B shows the coupling between the first and second cylinders 450 and 451 and the second annular baffle 425b. The cylinders 450 and 451 include a plurality of sealant holes 445. Each of the annular baffles 425 includes a plurality of baffle channels 435. The coupling between the first and second cylinders 450 and 451 and the second annular baffle 425b includes injecting a sealing material into the sealant holes 445 of the annular baffles 445. The sealing material flows through the sealant holes 445 of the annular baffles 425 and around any hollow fibers passing through the annular baffles 445 thereby forming an internal seal around the hollow fibers and securing the hollow fibers to the annual baffles 445. The plurality of baffle channels 435 of the annular baffles 425 direct the flow of the injected sealing material as it forms an internal seal around the hollow fibers in the module 301 and minimizes wicking of the injected sealing material. The sealing material secures the hollow fibers in the module 301 and creates an internal seal around the hollow fibers thereby minimizing sealing issues such as residual air-pockets. In some implementations, the sealing material is R36 epoxy. In some implementations, the entirety of the module 301 may be manufactured from one or more plastic materials. In some implementations, the plastic material may include PETG, polycarbonate and/or polystyrene.

Figure 5A:
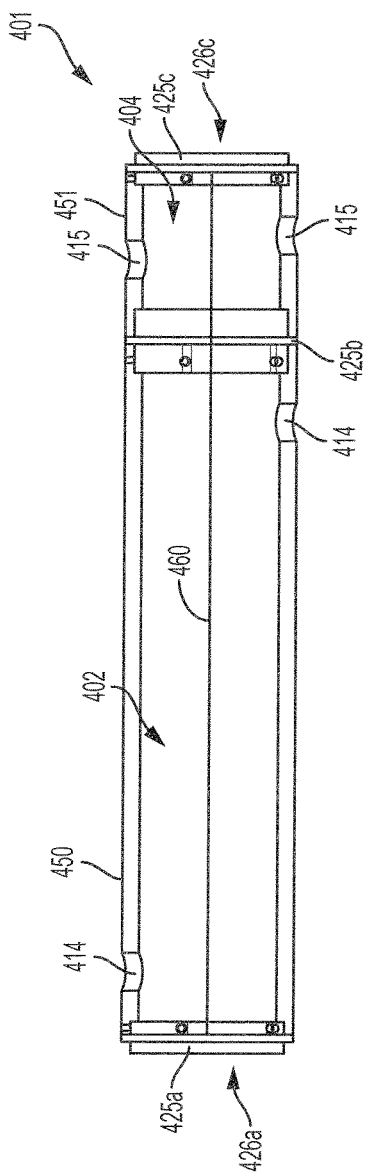
FIG. 5A illustrates a side view of the example module illustrated in FIGS. 4A and 4B.
Figure 5B:
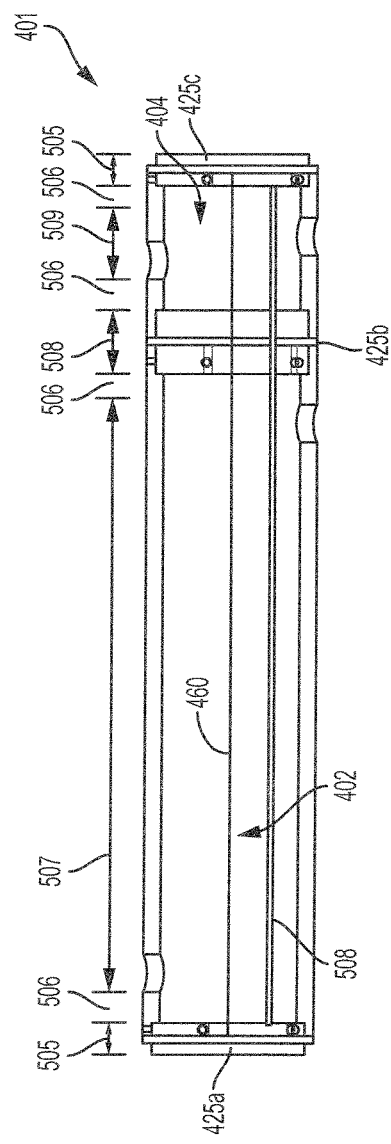
FIG. 5B illustrates the example module in FIG. 5A showing the dimensions of the example module.

FIG. 5A illustrates a cross sectional view of the module 301 illustrated in FIGS. 4A and 4B. In some implementations, each of the first and second cylinders 450 and 451 may be manufactured as two half cylinders which are adhered face-to-face to each other at an interface 460 to form a full cylinder. FIG. 5B illustrates a cross sectional view of the module 301 illustrating the dimensions of the module 301. For illustrative purposes, the module 301 includes a single hollow fiber 508. In some implementations, the lengths 505 of the annular baffles 425 can be between about 0.5 mm and about 3.5 cm or between about 0.5 cm and about 2.5 cm. Tight tolerances around the annular baffles 425 may act as a positive alignment feature for aligning and sealing the first and second cylinders 450 and 451. In some implementations, installing a plurality of hollow fibers 508 into the module 301 may render a portion of the hollow fibers 508 unusable for filtering or infusing the blood that passes through them. For example, portions of the hollow fibers 508 may be coated or clogged with an adhesive or sealant at locations where the hollow fibers are sealed into the baffles. In some implementations, the length 507 of the portion of the hollow fibers 508 that is usable for blood filtration may be between about 10 cm to about 15 cm, e.g., about 12.5 cm. In some implementations, the length 509 of the portion of the hollow fibers 508 that is usable for blood infusion may be between about 1.25 cm to about 2.5 cm, e.g. about 1.9 cm. In some implementations, the lengths 506 of the portions of the hollow fibers 508 that are unusable for blood filtration or blood infusion may be about between about 0.125 cm and about 0.50 cm, e.g. about 0.32 cm. In some implementations, the total length 508 of the second annular baffle 425b may be between about 0.75 cm to about 1.8 cm, e.g. about 1.25 cm. In some implementations, the length 505 of the first and third annular baffles 425a and 425c may be between about 0.25 cm and about 0.75 cm, e.g. about 0.65 cm. In some implementations, the face-to-face length 501 of the module 301 including gaps to allow for machining tolerances may be between about 16.5 cm and 21.5 cm, e.g. about 18.5 cm. In some implementations, the length of the portions of the hollow fibers 508 including the portion usable for blood filtration and the portion usable for blood infusion may be between about 15.25 cm to about 20.5, e.g. about 18.5 cm. In some implementations, the length of the hollow fibers 508 in a module 301 may be between about 20.32 cm to about 25.5 cm, e.g. about 23 cm.

In some implementations, the hemofiltration devices described herein may include a plurality of hollow fiber sub-bundles passing through the filtrate and infusion chambers. FIGS. 6A and 6B illustrate an example module 601 configured for a plurality of hollow fiber sub-bundles. The module 601 is substantially similar to the module 301 shown in FIGS. 4A and 4B with the exception that the module 601 includes a plurality of baffles, such as a first baffle 625a, a second baffle 625b and a third baffle 625c (collectively referred to as baffles 625) that are configured for routing a plurality of hollow fiber sub-bundles through the module 601. The faces 609a, 609b and 609c (collectively referred to as the faces 609) of the baffles 625 include a plurality of holes 611. For illustrative purposes, the module 601 shows a single hollow fiber sub-bundle 608 running along the length of the module 601 and passing through the first chamber 602, the holes 611 of the third baffle 625c and into and through the second chamber 604. FIG. 6B illustrates an enlarged view of a portion 685 of the example module 601 illustrated in FIG. 6A. In FIG. 6B, the ends of the hollow fiber sub-bundles 608 are aligned with and end at the holes 611 of the first baffle 625a. In some implementations, the ends of the hollow fiber sub-bundles 608 may not align exactly with and end at the holes 611 of the baffles 625 on each end of the module 601. For example, a portion of the hollow fiber sub-bundles 608 may extend through the holes 611 of the baffles 625.

Figure 7:
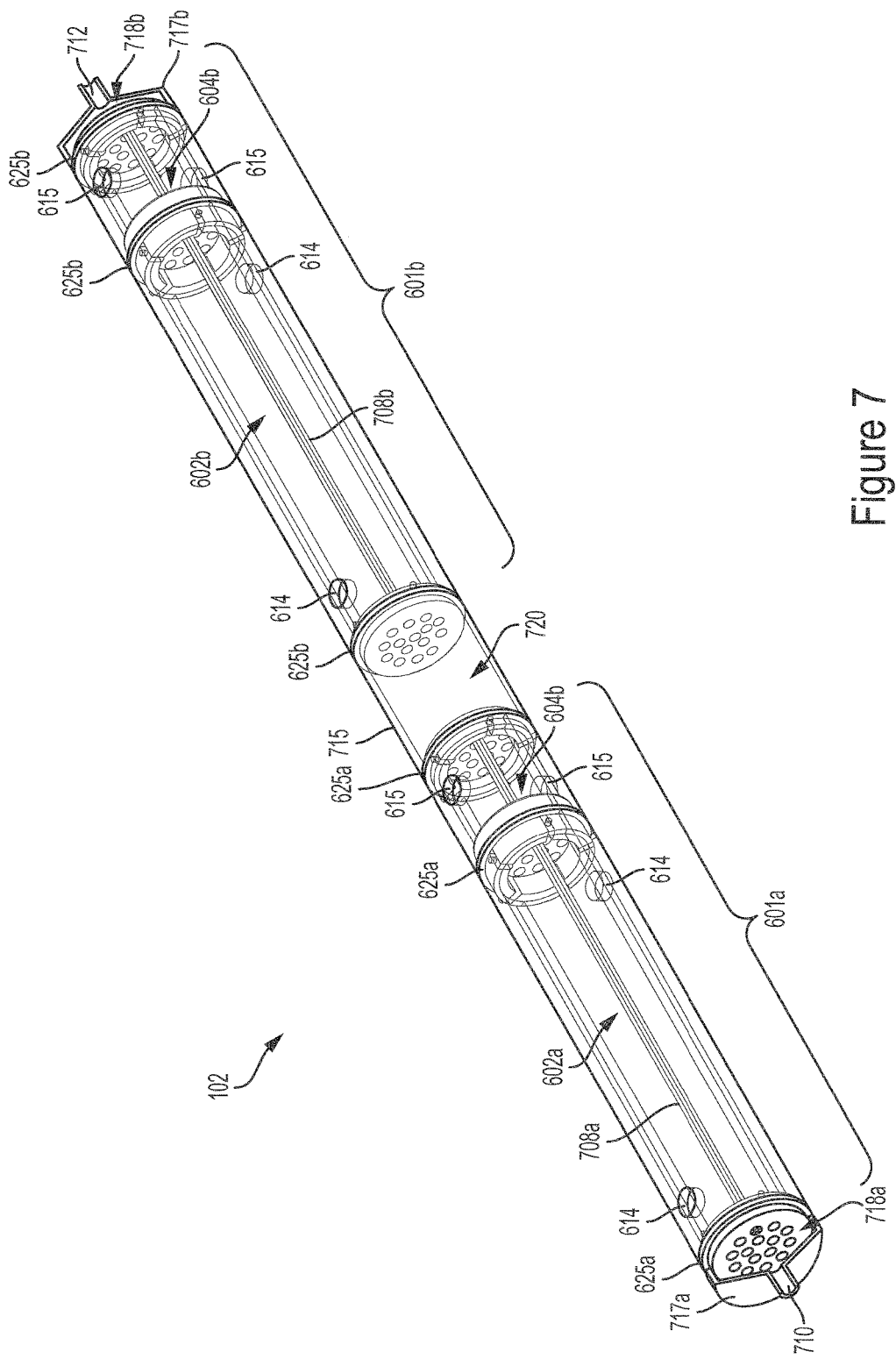
FIG. 7 illustrates a perspective view of an example hemotransfiltration device implemented using the module illustrated in FIGS. 6A and 6B and suitable for use in the system illustrated in FIG. 1.

FIG. 7 illustrates a perspective view of an example hemotransfiltration device 700 suitable for use as the hemofiltration device 102 in the system 100 and implemented using the module 601 shown in FIG. 6 FIGS. 6A and 6B. The hemotransfiltration device 700 includes a first module 601a and a second module 601b (collectively referred to as modules 601). The first module 601a includes a first filtrate chamber 602a and a first infusate chamber 604a. The second module 601a includes a second filtrate chamber 602b and a second infusate chamber 604b. The device 700 includes a mixing module 715. The mixing module 715 is located between the first module 601a and the second module 601b. The mixing module 715 defines a mixing chamber 720. The first filtration chamber 602a, the first infusate chamber 604a, the mixing chamber 720, the second filtration chamber 602b and the second infusate chamber 604b are distributed along the length of the device 700. In some implementations, the mixing module 715 may define multiple mixing chambers.

Although the device 700 is shown having two chamber modules 601a and 601b, the device 700 can include any number of chamber modules 601 serially connected along the length of the device 700. In some implementations, the chamber modules 601 may be arranged such that each of the infusate chambers 604 is followed by a respective filtrate chamber 602 along the length of the housing of the device 700. In some other implementations, the device 700 may include a first chamber that serves as an infusate chamber 604 to pre-dilute the blood in the hollow fibers prior to the blood entering the first filtrate chamber 602. In some implementations, the hemotransfiltration device 700 includes between about one about and about ten filtrate chambers 602, between about one and about eight filtrate chambers 602, or between about three and about six filtrate chambers 602. In some implementations, the number of filtrate chambers 602 may be different from the number of infusate chambers 604. For example, in some implementations, a first module of the hemofiltration device 700 may include two infusion chambers separated by a filtrate chamber so that blood can be pre-diluted prior to entering the first filtration chamber.

The hemofiltration device 702 includes a first endcap 717a and a second endcap 717b (collectively referred to as endcaps 717), each located at opposite ends of the device 700. The first endcap 717a includes an inlet 710 and the second endcap 717b includes an outlet 712. Blood enters the hemotransfiltration device 700 through the inlet 710 of the first endcap 717a and exits the device 700 through the outlet 712 of the second endcap 717b.

The hemotransfiltration device 700 includes a first set of hollow fiber sub-bundles 708a in the first module 601a and a second set of hollow fiber sub-bundles 708b in the second module 601b. For illustrative purposes, the first set and the second set of hollow fiber sub-bundles 708a and 708b each shows only one hollow fiber sub-bundle. The first set of hollow fiber sub-bundles 708a run along the length of the first chamber module 601a and pass through the first filtrate chamber 602a and the first infusate chamber 604a. The second set of hollow fiber sub-bundles 708b run along the length of the second chamber module 601b and pass through the second filtrate chamber 602b and the second infusate chamber 604b.

In some implementations, the hemotransfiltration device 700 can include between about 1,000 and about 50,000 hollow fibers, between about 1,000 and about 35,000 hollow fibers, between about 5,000 and about 20,000 hollow fibers or between about 6,000 and 15,000 hollow fibers. In some implementations, each hollow fiber sub-bundles 708a and 708b may include between about 10 hollow fibers and about 300 hollow fibers. In some implementations, each of the hollow fiber sub-bundles 708a and 708b have a length between about 5 cm and about 80 cm, between about 20 cm and about 70 cm, or between about 30 cm and about 60 cm.

The walls of the hollow fibers in each of the hollow fiber sub-bundles 708a and 708b are configured to enable fluid and solutes to pass from the blood and into the filtrate within the filtrate chambers 602 and infusate into the hollow fibers in each of the hollow fiber sub-bundles 708a and 708b within the infusate chambers 604. In some implementations, the wall of the hollow fibers in each of the hollow fiber sub-bundles 708a and 708b is between about 20 µm and about 75 µm or between about 30 µm and about 50 µm thick. Each of the hollow fibers in the hollow fiber sub-bundles 708a and 708b have an inner diameter between about 50 µm and about 300 µm or between about 100 µm and about 250 µm.

As shown in FIG. 7, the first set of hollow fiber sub-bundles 708a runs through the first chamber module 601a with each end of the first set of hollow fiber sub-bundles 708a aligning with and ending at the holes 611 of the baffles 625a that are coupled to each end of the first chamber module 601a. The second set of hollow fiber sub-bundles 708b runs through the second chamber module 601b with each end of the second set of hollow fiber sub-bundles 708b aligning with and ending at the holes 611 of the baffles 625b that are coupled to each end of the second chamber module 601b. The first and second set of hollow fibers sub-bundles 708a and 708b do not pass through the mixing chamber 720.

Blood enters the hemotransfiltration device 700 through the inlet 710 of the first endcap 717a and passes through the first set of hollow fiber sub-bundles 708a running along the length of the first chamber module 601a. As the blood flows through the first set of hollow fibers 708a in the first filtration chamber 602a, fluid and solutes are removed from the blood through convective clearance. As the blood flows through the first set of hollow fibers 708a in the infusion chamber 604a, clean fluid is infused through the walls of the first set of hollow fibers 713 and into the blood.

The blood exits from the first set of hollow fiber sub-bundles 708a at the distal end of the first infusate chamber 604a and flows into the mixing chamber 720. The blood mixes in the mixing chamber 720 and passes into the second set of hollow fibers 708b running along the length of the second chamber module 601b. The mixing chamber 720 facilitates the mixing of blood as it flows from the first set of hollow fibers sub-bundles 708a into the second set of hollow fiber sub-bundles 708b. As shown in FIG. 7, the open ends of the first set of hollow fiber sub-bundles 708a align with and end at the holes 611 of the baffles 625a. The blood flows through and out of each of the hollow fibers in the first set of hollow fiber sub-bundles 708a and flows into the mixing chamber 720. The blood mixes within the mixing chamber 720 before it enters the second set of hollow fiber sub-bundles 708b. Thus the mixing chamber 720 facilitates the mixing of blood flowing out of each hollow fiber of the first set of hollow fiber sub-bundles 708a to mix together along the length of the mixing chamber 720 before the blood enters the second set of hollow fiber sub-bundles 708b. In some implementations, the mixing module 715 may define a plurality of mixing chambers. Each mixing chamber may correspond to a sub-bundle of the first set of hollow fiber sub-bundles 708a. The blood flows through and out of the hollow fibers of each sub-bundle and enters a corresponding mixing chamber. Thus, the blood from all of the hollow fibers in each sub-bundle is able to mix along the length of a corresponding mixing chamber.

As the blood flows through the second set of hollow fiber sub-bundles 708b in the second filtration chamber 602b, fluid and solutes are removed from the blood through convective clearance. As the blood flows through the second set of hollow fiber sub-bundles 708b in the second infusate chamber 604b, clean fluid is infused through the walls of the second set of hollow fiber sub-bundles 708b and into the blood. The blood flows from the second set of hollow fiber sub-bundles 708b in the second infusate chamber 604b and exits the device 700 through the outlet 712 of the second endcap 717b. In some implementations, the first endcap 717a may define a first plenum 718a located between the first endcap 717a and the opening of the first chamber module 701a. In such implementations, the blood enters the device 700 through the inlet 710 of the first endcap 717a and mixes within the first plenum 718a before passing into and through the first set of hollow fiber sub-bundles 708a in the first filtrate chamber 702a of the first chamber module 701a. In some implementations, the second endcap 717b may define a second plenum 718b located between the second endcap 717b and the opening of the second chamber module 701b. In such implementations, the blood passes through and out of the second set of hollow fiber sub-bundles 708b in the second infusate chamber 702b of the second chamber module 701b and mixes within the second plenum 718b before exiting the device 700 through the outlet 712 of the second endcap 717b. In some implementations, the lengths of the first and second plenum 718a and 718b may be between about 1 mm to about 2 cm.

Referring back to FIGS. 2, 3 and 7, in some implementations of the devices 200, 300 and 700, the length of the filtrate chambers 202, 302 and 702 and the length of the infusate chambers 204, 304 and 704 are related to the inner diameter of the hollow fibers passing through the chambers 204, 304 and 704. For example, smaller inner diameter sizes of the hollow fibers passing through the chambers 204, 304 and 704 can generate relatively higher flux through the walls of the hollow fibers passing through the chambers 204, 304 and 704. Because the flux is greater when the inner diameter of the hollow fibers passing through the chambers 204, 304 and 704 is smaller, the length of the filtrate chambers 202, 302 and 702 can be shorter in length compared to when the inner diameter of the hollow fibers passing through the chambers 204, 304 and 704 is larger. For example, if the hollow fibers passing through the filtrate chambers 202, 302 and 702 have an inner diameter of about 50 μm, the length of the filtrate chambers 202, 302 and 702 can be about 1.6 cm; if the hollow fibers passing through the filtrate chambers 202, 302 and 702 have an inner diameter of about 100 μm, the length of the filtrate chambers 202, 302 and 702 can be about 6 cm; if the hollow fibers passing through the filtrate chambers 202, 302 and 702 have an inner diameter of about 200 μm, the length of the filtrate chambers 202, 302 and 702 can be about 14 cm, and if the hollow fibers passing through the filtrate chambers 202, 302 and 702 have an inner diameter of about 300 μm, the length of the filtrate chambers 202 can be about 15 cm. In some implementations, the devices 200, 300 and 700 may be manufactured from one or more plastic materials. In some implementations, the plastic material may include PETG, polycarbonate and/or polystyrene.

Figure 8:
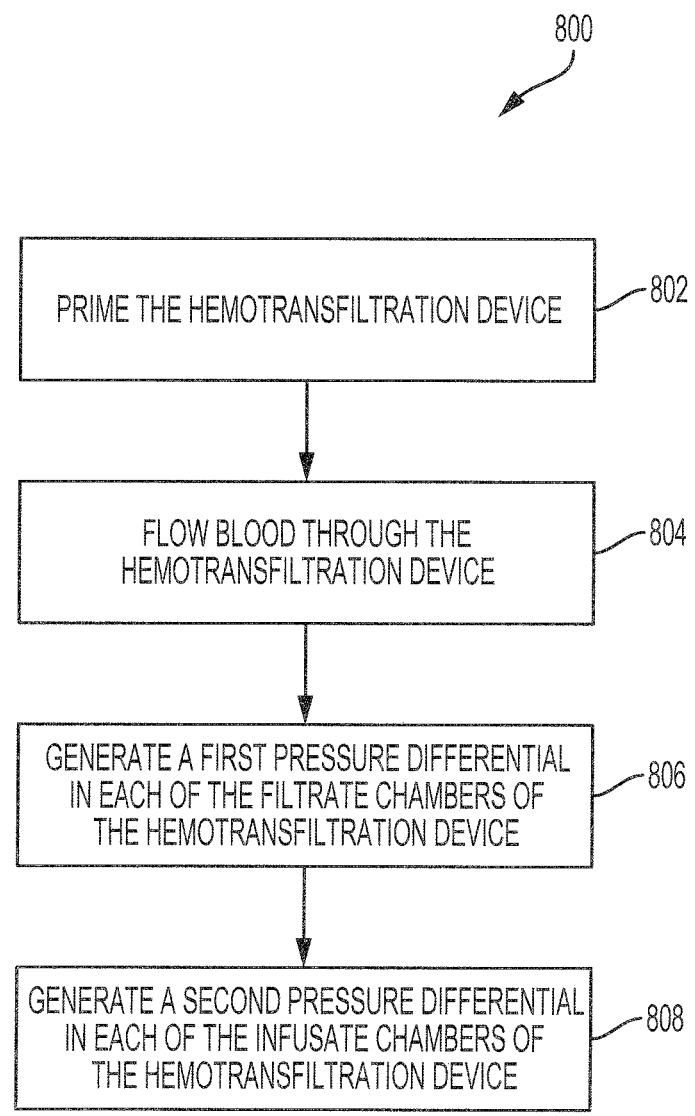
FIG. 8 illustrates a flow diagram of an example method for filtering blood using the system illustrated in FIG. 1.

FIG. 8 illustrates a flow diagram of an example method 800 for filtering blood using the hemotransfiltration devices described herein. The method 800 includes priming the hemotransfiltration device (step 802). The method also includes flowing blood through the hemotransfiltration device (step 804). A first pressure differential is generated in each of the filtrate chambers of the hemotransfiltration device (step 806). A second pressure differential is generated in each of the infusate chambers of the hemotransfiltration device (step 808).

As set forth above, and also referring to FIGS. 2, 3 and 7, the method 800 includes priming the hemotransfiltration device (step 302). As illustrated in FIGS. 2, 3 and 7, each of the filtrate chambers 202, 302 and 602 and the infusate chambers 204, 304 and 604 include two ports 214, 314, 614. When the chambers of the hemotransfiltration device 200, 300 and 700 are primed, one port 214, 314, 614 to each of the chambers is left open. The other port 214, 314, 614 is coupled to a respective infusion pump or filtration pump. As the filtrate is pumped into the filtrate chambers 202, 302 and 602 and the infusate into the infusate chambers 204, 304, 604, air can escape the chambers through the open ports 214, 314, 614. Once the chambers are primed, the open port is closed such that the flow rates into or out of the chambers are controlled through a single port.

The method 800 also includes flowing blood through the hemotransfiltration device (step 804). As described above in relation to FIGS. 1 and 2, 3 and 7, the blood pump 104 flows blood from a blood reservoir 110 (or patient) through the hemotransfiltration device 200, 300 and 700. Once the blood enters the hemotransfiltration device 200, 300 and 700 at the inlet 210, 310, 610, the blood disperses into one of a plurality of hollow fibers 208, 308 and 708a. As described above, the hollow fibers 208 and 308 run the length of the hemotransfiltration device 200 and 300 while a first set and second set of hollow fiber sub-bundles 708a and 708b run the length of the modules 601a and 601b of the hemotransfiltration device 700. Toward the end of the hemotransfiltration device 200, 300 and 700, the blood exits the hollow fibers 208, 308 and 708b and then exits the hemotransfiltration device 200, 300 and 700 through the outlet 212, 312 and 712. In some implementations, the blood pump 104 flows the blood through the hemotransfiltration device 200, 300 and 700 at a rate between about 0.01 ml/min/fiber and about 0.1 ml/min/fiber, between about 0.03 ml/min/fiber and about 0.08 ml/min/fiber, or between about 0.05 ml/min/fiber and about 0.08 ml/min/fiber.

The method 800 also includes generating a first pressure differential between the filtrate and the blood in each of the filtrate chambers of the hemotransfiltration device (step 806). In some implementations, the first pressure differential between the filtrate and the blood is between about 10 mmHg and about 500 mmHg, between about 50 mmHG and about 450 mmHg, between about 100 mmHg and about 400 mmHg, between about 150 mmHg and about 350 mmHG, or between about 150 mmHg and about 300 mmHg or between about 200 mmHg and about 300 mmHg or between about 100 mmHg and about 800 mmHg. The first pressure differential is generated such that the pressure in the filtrate chambers is less than the pressure of the blood in the hollow fibers. Once one of the ports to the filtrate chambers is sealed, the pressure differential is generated when the filtration pumps 108 drawing filtrate from each of their respective filtrate chambers. The pressure differential drives fluid and solutes from the blood into the filtrate of the filtrate chambers. In some implementations, each of the filtrate chambers are coupled to different filtration pumps and different pressure differentials are generated in each of the filtrate chambers. For example, the pressure differential in the first filtrate chamber can have a magnitude less than the pressure differential in the last filtrate chamber. In another example, the pressure differential in the first filtrate chamber can have a magnitude greater than the pressure differential in the last filtrate chamber. The method 800 also includes generating a second pressure differential between the infusate and the blood in each of the infusate chambers of the hemotransfiltration device (step 808). In some implementations, the second pressure differential between the infusate and the blood is between about 1 mmHg and about 1000 mmHg, between about 200 mmHg and about 800 mmHg, or between about 400 mmHg and about 600 mmHg or between about 1000 mmHg to about 1600 mmHg. The second pressure differential is generated such that the infusate pressure is greater than the blood pressure in each of the hollow fibers. In some implementations, the second pressure differential can be according to the following equation:

$$\text{Infusion } TMP(\text{mmHG}) = \frac{\sim 88{,}000 * \text{infusion rate}\left(\frac{\text{ml}}{\text{min}}\right)}{(\text{number of hollow fibers}) * (\text{length of the infusate chamber (cm)})}$$

The pressure differential drives infusate through the walls of the hollow fibers and into the blood flowing through the hollow fibers. The infusate driven into the blood replenishes the fluid lost from the blood during the filtering phases (e.g., when the blood passes through the filtrate chambers). Replenishing the blood's fluid levels (also referred to as rehydrating the blood) enables a greater amount of solutes to be removed from the blood. Without rehydration of the blood, the loss of fluid can cause the blood to clot or cause other damage to the cells and other essential elements of the blood. By rehydrating the blood after each filtering stage, additional fluid (and thus solutes) can be removed from the blood during a subsequent filtering stage. For example, without rehydration only about 20% of the fluid volume can be removed from the blood before the concentration of formed elements (e.g., blood cells) is too high, which results in clotting and other complications. By alternatively filtering and rehydrating the blood, substantially all of the original fluid of the blood can be exchanged as the blood flows through the hemotransfiltration device. Additionally, by filtering and rehydrating the blood within a single device, the blood does not exit and then re-enter multiple fibers, which can lead to clotting and blood cell damage.

Referring back to FIGS. 2, 3 and 7, the transmembrane pressure (TMP) for the hollow fibers in the device 200, 300 and 700 in the filtrate chambers 202, 302 and 602 and the infusate chambers 204, 304 and 604 depends on the blood flow rate through the hollow fibers and the length of the hollow fibers. The measured transmembrane pressure (TMP) for the hollow fibers in an infusate chamber or a filtrate chamber depends on the blood flow rate through the hollow fibers and the length of the hollow fibers. For a given TMP, the blood flow rate through the hollow fibers scales accordingly with the number of hollow fibers. Also, the measured TMP is inversely proportional to the length of the hollow fibers. For example, if the blood flow rate (Qb) is about 0.374 ml per minute for each hollow fiber 208, the exposed or usable hollow fiber length in the filtrate chamber is about 12.7 cm, the exposed or usable hollow fiber length in the infusate chamber is about 1.9 cm, the filtrate fraction in a single filtrate chamber is about 25% and the infusate fraction in a single infusion chamber is about 33% then the measured filtrate TMP for the hollow fibers 208 is between about 50 mmHg and about 1000 mmHg, between about 150 mmHg and about 600 mmHg or between about 200 mmHg and 450 mmHg. In this example, the measured infusate TMP for the hollow fibers 208 is between about 1500 mmHg and about 3500 mmHg or between about 1800 mmHg and about 2500 mmHg.

Figure 14:
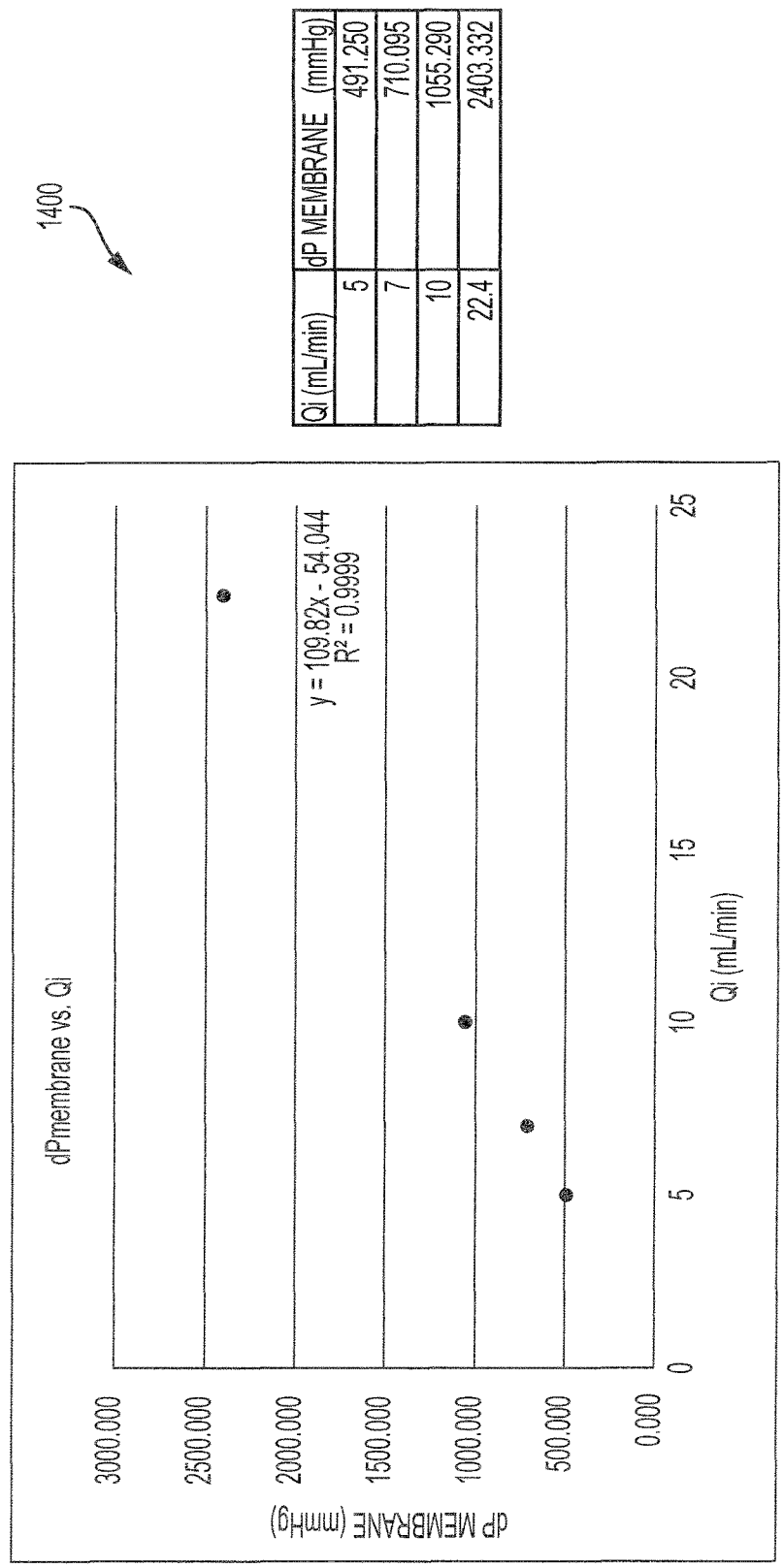
FIG. 14 illustrates a graph that shows the measured transmembrane pressure (TMP) within a range of flow rates of blood in the hollow fibers in an infusate chamber of an example hemotransfiltration device.

FIG. 14 illustrates a graph 1400 that shows the measured transmembrane pressure (TMP) within a range of flow rates of blood in the hollow fibers in an infusate chamber of an example hemotransfiltration device.

Figure 15:
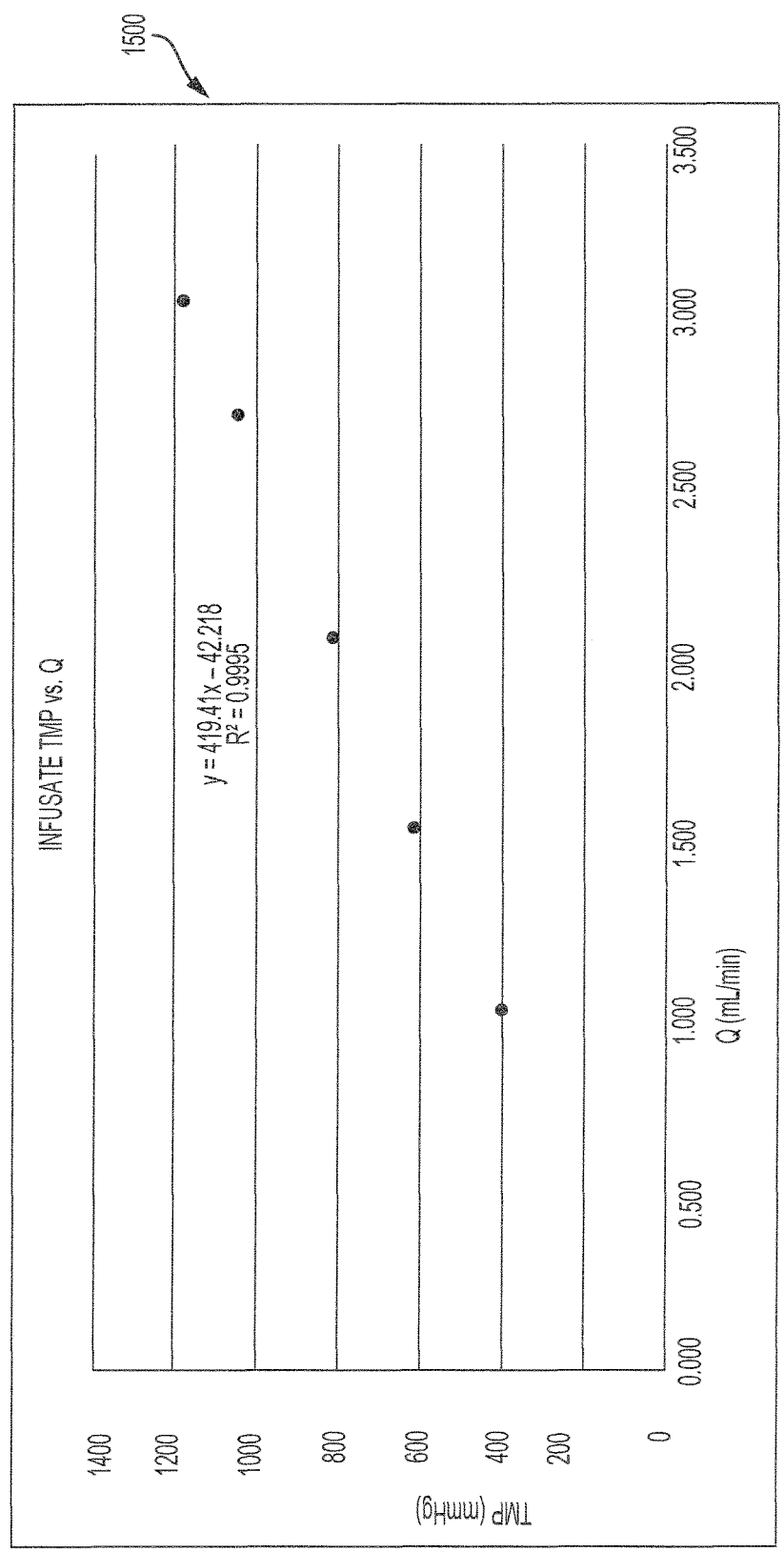
FIG. 15 illustrates a graph that shows the measured transmembrane pressure (TMP) within a range of flow rates of blood in the hollow fibers in an infusate chamber of an example hemotransfiltration device.

FIG. 15 illustrates a graph 1500 that shows the measured transmembrane pressure (TMP) within another range of flow rates of blood in the hollow fibers in an infusate chamber of an example hemotransfiltration device. The infusate chamber includes a total of about 300 hollow fibers having a length between about 2.1 cm and about 2.3 cm, such as about 2.2 cm.

Experimental data gathered from the hemofiltration devices described herein indicates that the measured infusate TMP for the hollow fibers is generally five times the measured filtrate TMP. Therefore, given a measured filtrate TMP of between about 200 mmHg and 300 mmHg, the measured infusate TMP may be between about 1000 mmHG and about 1600 mmHG.

Figure 9:
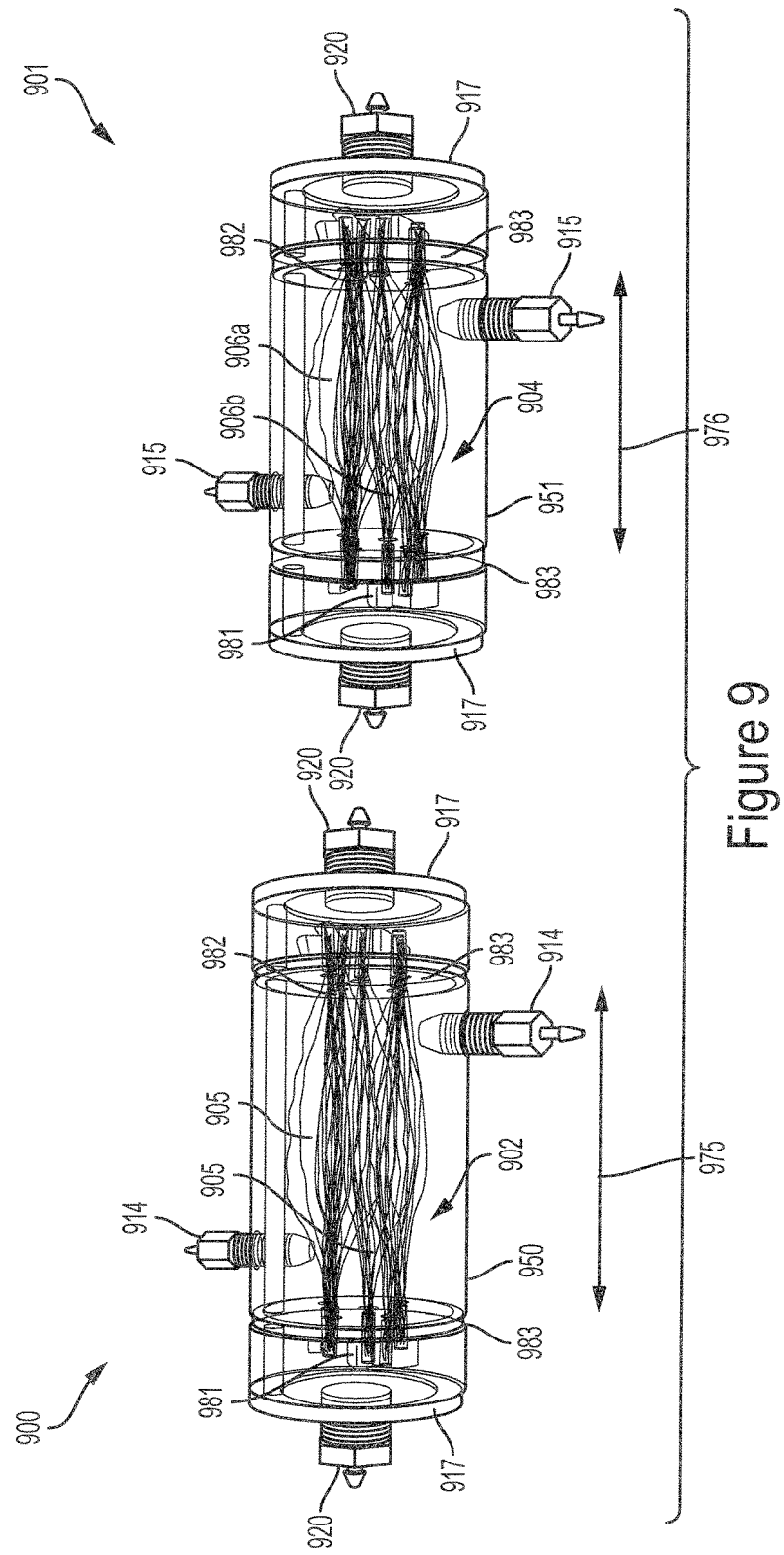
FIG. 9 illustrates a perspective view of two example modules for use in a hemotransfiltration device.

As mentioned above, the example hemotransfiltration devices 300 and 700 may be implemented with two-chamber modules such as the modules 301 and 601. In some implementations, an example hemofiltration device may be implemented with a plurality of single-chamber modules. FIG. 9 illustrates a perspective view of two example single-chamber modules 900 and 901 for use in an implementation of a hemotransfiltration device suitable for use as the hemotransfiltration device 102 in the system 100 shown in FIG. 1. The housing of the first example single-chamber module 900 includes a hollow open-ended cylinder 950. Each end of the cylinder 950 is coupled to an endcap 917. The cylinder 950 includes a chamber 902. The cylinder 950 includes a pair of ports 914 that enable fluid to enter and exit the chamber 902. Each endcap 917 includes a port 920 that enables fluid to enter or exit the module 900 via the endcap 917. The module 900 also includes a plurality of hollow fiber sub-bundles 905 running along the length of the cylinder 950 and passing through the chamber 902.

The module 901 is substantially similar to the module 900 with the exception of the length of the chamber housing. The housing of the module 901 is a hollow open-ended cylinder 951 that includes a chamber 904. The length 976 of the cylinder 951 of the module 901 is shorter than the length 975 of the cylinder 950 of the module 900. The module 901 includes a plurality of hollow fiber sub-bundles 906 running along the length of the cylinder 951 and passing through the chamber 904.

An example implementation of a hemotransfiltration device described herein may include a plurality of filtrate and infusate segments distributed along a length of the device. Each of the infusate segments is positioned after one of the filtrate segments. The infusate segments may be implemented by the module 901 and the filtrate segments may be implemented by the module 900.

Figure 10:
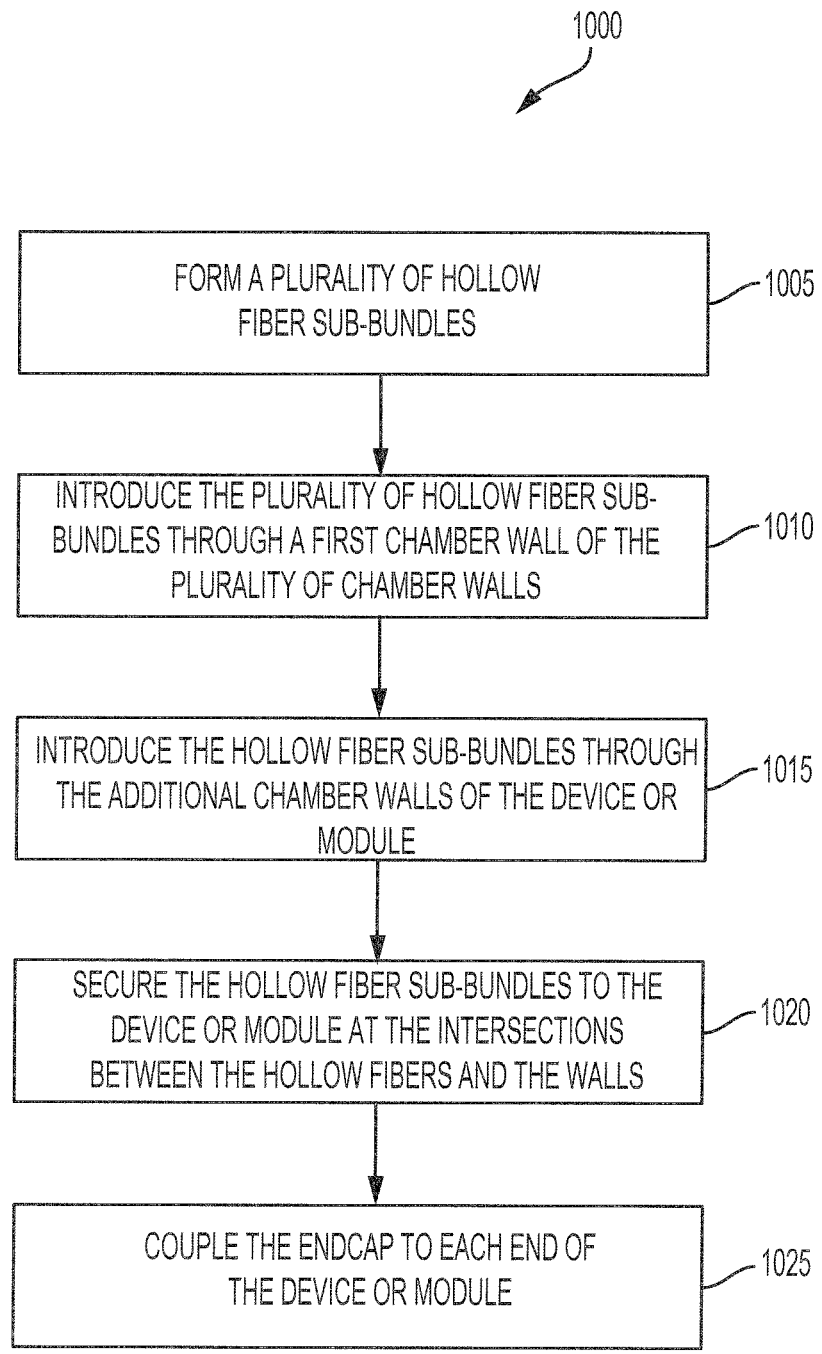
FIG. 10 illustrates a flow diagram of an example method 1000 for assembling a hemotransfiltration device.

FIG. 10 illustrates a flow diagram of an example method 1000 for assembling a hemotransfiltration device or module. The method 1000 includes forming a plurality of hollow fiber sub-bundles (step 1005). The method 1000 includes introducing the plurality of hollow fiber sub-bundles through a first chamber wall of the plurality of chamber walls (step 1010). The method 1000 includes introducing the hollow fiber sub-bundles through the additional chamber walls of the device or module (step 1015). The method 1000 includes securing the hollow fiber sub-bundles to the device or module at the intersections between the hollow fibers and the walls (1020). The method 1000 includes coupling an endcap to each end of the device or module (step 1025).

Figure 11:
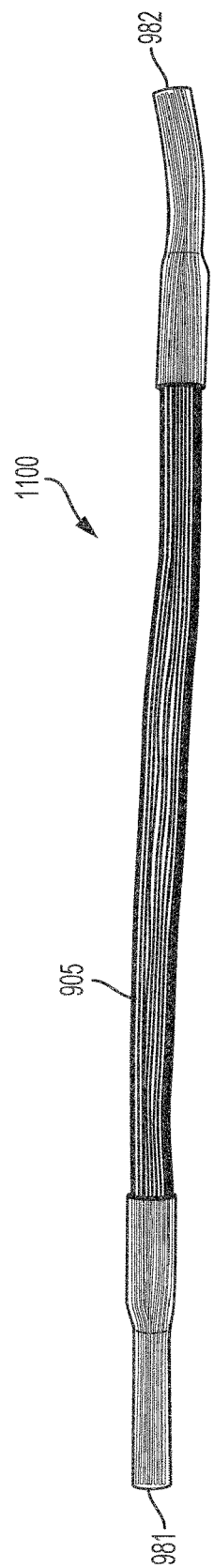
FIG. 11 illustrates a side view of an example hollow fiber sub-bundle for use in the modules illustrated in FIG. 9.

The method 1000 includes forming a plurality of hollow fiber sub-bundles (step 1005). Forming each hollow fiber sub-bundle includes securing a plurality of hollow fibers at each end. In some implementations, the ends of each hollow fiber sub-bundle may be secured by a sealing material such as epoxy. As shown in FIG. 9, each of the hollow fiber sub-bundles 905 and 906 of the modules 900 and 901 is formed by routing the sub-bundle through two pieces of shrink tube 981 and 982 such that the two pieces of shrink tube 981 and 982 are located at opposite ends of the sub-bundle. Shrinking each of the shrink tubes 981 and 982, for example by applying heat, secures the hollow fibers of the sub-bundle within the shrink tubes 981 and 982. FIG. 11 illustrates a top view of one hollow fiber sub-bundle 1100 of the plurality of hollow fiber sub-bundles 905 and 906 shown in FIG. 9. The hollow fiber sub-bundle 1100 includes a plurality of hollow fibers secured at the ends by a first shrink tube 981 and a second shrink tube 982.

The method 1000 includes introducing the plurality of hollow fiber sub-bundles through a first chamber wall of the plurality of chamber walls (step 1010). In some implementations, the first chamber wall may be a disc with a plurality of holes. In FIG. 9, assembling the modules 900 and 901 includes threading each end of the hollow fiber sub-bundles 905 and 906 through one of a plurality of holes in a first PETG disc 983. In some implementations, the first wall may be a potting compound or a fixed wall already integrally formed with or adhered into a cylindrical chamber. In FIG. 2, assembling the device 200 includes introducing the plurality of hollow fibers 208 through the first wall 206. In some implementations, the wall may be a baffle that includes a face with a plurality of holes. In FIG. 7, assembling the device 700 includes introducing the hollow fiber sub-bundles 708 through the holes 611 of the first baffle 625a.

Figure 12:
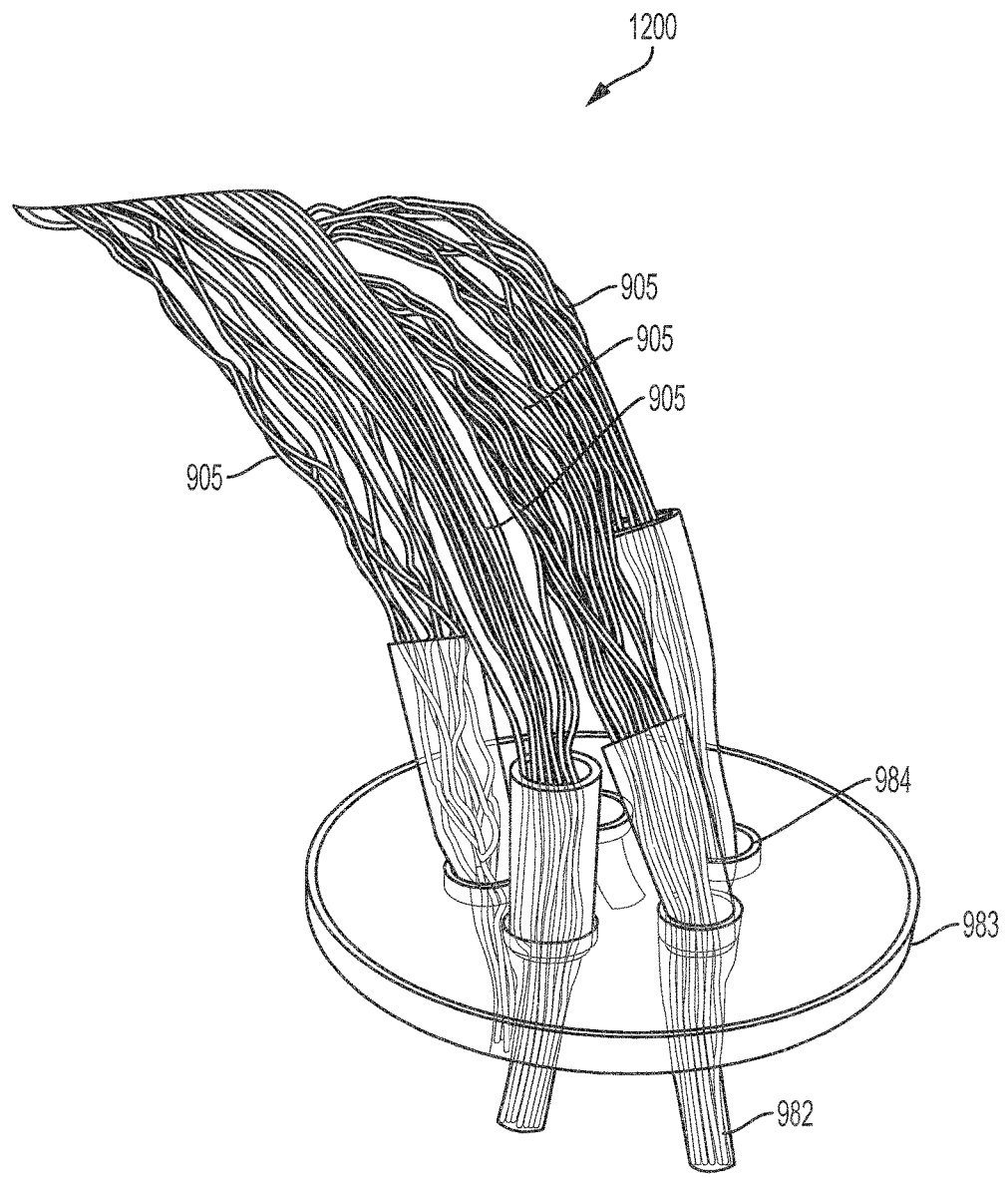
FIG. 12 illustrates a perspective view of a plurality of hollow fiber sub-bundles routed through a first wall of a module shown in FIG. 9.

The method 1000 includes introducing the hollow fiber sub-bundles through the additional chamber walls of the device or module (step 1015). In some implementations, such as the device 200 in FIG. 2, the hollow fiber sub-bundles 208 are routed through the additional walls 206 of the device 200 thereby routing the hollow fibers 208 through the filtrate and infusate chambers 202 and 204. In some implementations, such as the module 601 in FIG. 6A, the hollow fiber sub-bundles are routed through the holes 611 of the second baffle 625b and the third baffle 625c. In some implementations, such as the modules 900 and 901 in FIG. 9, each end of the hollow fiber sub-bundles 905 and 906 is routed through the cylinders 950 and 951 such that the hollow fiber sub-bundles 905 and 906 pass through the chambers 902 and 904 of the cylinders 950 and 951. The first disc 983 of each module 900 and 901 is coupled to one end of their respective cylinders 950 and 951 and each end of the hollow fiber sub-bundles 905 and 906 covered by the second shrink tube 982 is routed through one of a plurality of holes in a second disc 983. The second disc 983 of each module 900 and 901 is coupled to one end of the respective cylinders 950 and 951. FIG. 12 illustrates a perspective view 1200 of the ends of the hollow fiber sub-bundles 905 covered by the shrink tube 982 threaded through the holes 984 of a disc 983.

Figure 13B:
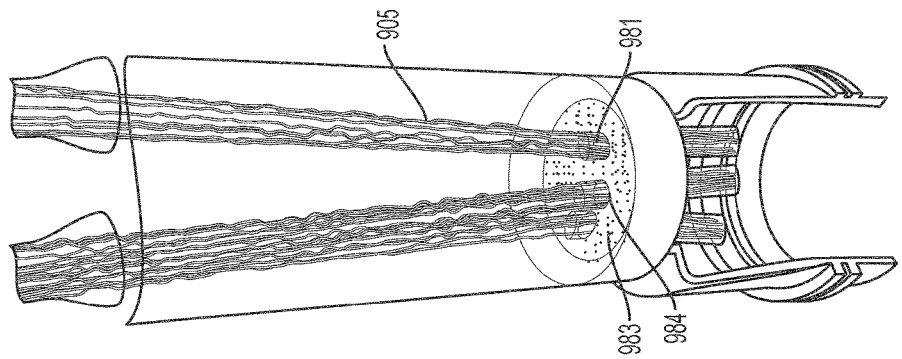
FIG. 13B illustrates the hollow fiber sub-bundles after securing the hollow fiber sub-bundles in the device or module as shown in FIG. 13A.
Figure 13A:
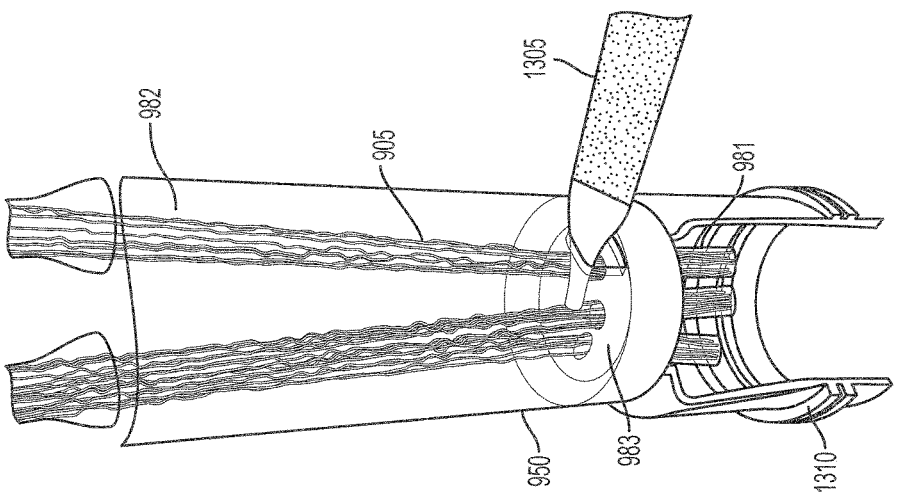
FIG. 13A illustrates securing the hollow fiber sub-bundles in the device or module according to the method illustrated in FIG. 10.

The method 1000 includes securing the hollow fiber sub-bundles in the device or module at the intersections between the hollow fibers and the walls (1020). In some embodiments, securing the hollow fiber sub-bundles includes the application of a sealing material to the hollow fibers at the intersection between the hollow fibers and the walls. As shown in FIGS. 13A and 13B, the hollow fiber sub-bundles 905 may be secured by injecting a large bolus of epoxy 1305 into the center of the disc 983 between the hollow fiber sub-bundles 905 and allowing the epoxy 1305 to flatten and spread across the disc 983 thereby surrounding the hollow fibers of the hollow fiber sub-bundles 905 and securing the hollow fiber sub-bundles 905 to the disc 983.

The method 1000 includes coupling an endcap to each end of the device or module (step 1025). Each of endcap includes a port that enables fluid to enter or exit the device or module.

The disclosed system and methods may be embodied in other specific forms without departing from the spirit or essential characteristics thereof. The forgoing implementations are therefore to be considered in all respects illustrative, rather than limiting of the invention.

What is claimed:

1. A blood filtration device comprising:
    a housing having an upstream end and a downstream end;
    at least three filtrate chambers distributed along a length of the housing;
    at least three infusate chambers, each of the at least three infusate chambers positioned downstream from a corresponding one of the at least three filtrate chambers along a length of the housing;
    a plurality of hollow fibers running along the length of the housing, the plurality of hollow fibers passing through the at least three filtrate chambers and the at least three infusate chambers; and
    a plurality of walls, wherein each wall separates one of the at least three filtrate chambers from one of the at least three infusate chambers and prevents passage of fluid between the separated chambers except through the plurality of hollow fibers.

2. The device of claim 1, each of the three filtrate chambers is separated from another of the three filtrate chambers by one of the at least three infusate chambers.

3. The device of claim 1, wherein each wall includes a plurality of holes.

4. The device of claim 3, comprising a plurality of hollow fiber sub-bundles, each hollow fiber sub-bundle including a subset of the plurality of hollow fibers.

5. The device of claim 4, wherein each hollow fiber sub-bundle passes through one of the holes in at least one of the walls.

6. The device of claim 4, wherein the hollow-fiber sub-bundles each include between about 10 and about 300 hollow fibers.

7. The device of claim 1, wherein:
    the plurality of hollow fibers includes a first set of hollow fibers and a second set of hollow fibers;
    the device comprises at least one mixing chamber positioned between one filtrate chamber and one infusate chamber;
    at least one of the at least three filtrate chambers and at least one of the at least three infusate chambers is located upstream from the mixing chamber;
    at least one of the at least three filtrate chambers and at least one of the at least three infusate chambers is located downstream from the mixing chamber;
    the first set of hollow fibers passes through the at least one filtrate chamber and the at least one infusate chamber located upstream from the mixing chamber; and
    the second set of hollow fibers passes through the at least one filtrate chamber and the at least one infusate chamber located downstream from the mixing chamber.

8. The device of claim 7, wherein the plurality of hollow fibers within each set of hollow fibers includes between about 1,000 and about 6,000 hollow fibers.

9. The device of claim 1, wherein each of the filtrate chambers are between about 1 cm and about 20 cm long.

10. The device of claim 1, wherein each of the infusate chambers are between about 0.1 cm and about 5 cm long.

11. The device of claim 1, wherein each of the plurality of hollow fibers comprises a permeable wall.

\* \* \* \* \*